United States Patent [19]  
Trenkle et al.

[11] 4,311,754
[45] Jan. 19, 1982

[54] PROCESS FOR HYDROGENATION OF 2,6,6-TRIMETHYL CYCLOHEXENE DERIVATIVES AND ORGANOLEPTIC USES OF SAID PRODUCTS

[75] Inventors: Robert W. Trenkle, Bricktown; Braja D. Mookherjee; Frederick L. Schmitt, both of Holmdel; Manfred H. Vock, Locust; Joaquin F. Vinals, Red Bank, all of N.J.; Jacob Kiwala, Brooklyn, N.Y.

[73] Assignee: International Flavors & Fragrances Inc., New York, N.Y.

[21] Appl. No.: 239,051

[22] Filed: Feb. 27, 1981

Related U.S. Application Data

[62] Division of Ser. No. 969,852, Dec. 15, 1978, Pat. No. 4,292,447.

[51] Int. Cl.$^3$ .................. B32B 33/00; D04H 1/40
[52] U.S. Cl. .................. 428/284; 428/905; 252/8.6; 252/522 R; 252/109; 252/173; 131/276; 426/590; 426/599; 424/70; 424/73

[58] Field of Search .................. 252/8.6; 428/284, 905

[56] References Cited

U.S. PATENT DOCUMENTS

| | | | |
|---|---|---|---|
| 3,589,372 | 6/1971 | Theimer | 131/276 |
| 3,632,396 | 1/1972 | Perez-Zamora | 428/291 |
| 3,956,392 | 5/1976 | de Haan et al. | 252/522 R |
| 4,065,408 | 12/1977 | Evers et al. | 252/522 R |
| 4,076,749 | 2/1978 | Schreiber | |

Primary Examiner—Maria Parrish Tungol
Attorney, Agent, or Firm—Arthur L. Liberman

[57] ABSTRACT

Described is a process for preparing hydrogenated derivatives of 2,6,6-trimethyl cyclohexene derivatives by means of treating said derivatives with hydrogen in the presence of a supported palladium catalyst such as palladium-on-calcium carbonate or palladium-on-barium sulfate in the presence of a quinoline activator. The resulting products are useful for their organoleptic properties as foodstuff flavorants and flavor enhancers, perfume composition ingredients, perfumed article ingredients and tobacco flavorants and flavor enhancers.

2 Claims, 19 Drawing Figures

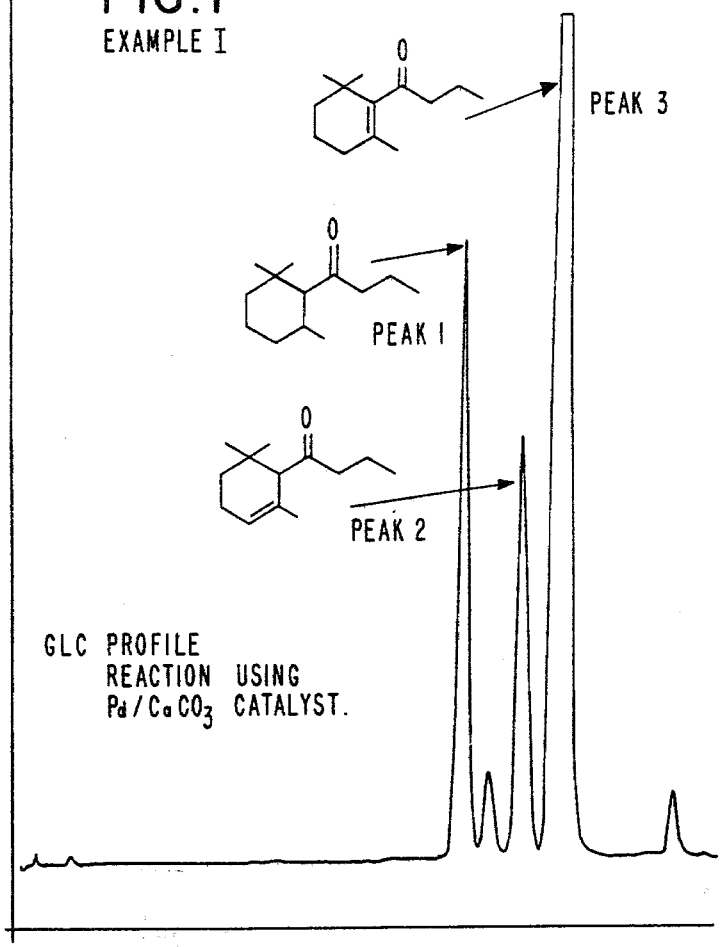
FIG. 1
EXAMPLE I
PEAK 3
PEAK 1
PEAK 2
GLC PROFILE
REACTION USING
Pd/CaCO$_3$ CATALYST.
FIG. 2
EXAMPLE I
PEAK 1
1-BUTYRYL-2,2,6 TRIMETHYL CYCLOHEXANE
MASS SPECTRUM
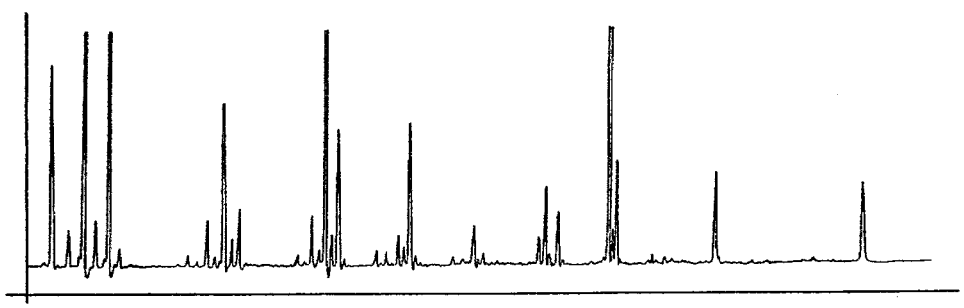

IR SPECTRUM FOR EXAMPLE I, PEAK I.

NMR SPECTRUM FOR EXAMPLE I, PEAK I.

EXAMPLE I
PEAK 2
1-BUTURY-2,2,6 TRIMETHYL-CYCLOHEX-5-ENE
MASS SPECTRUM

IR SPECTRUM FOR EXAMPLE I, PEAK 2.

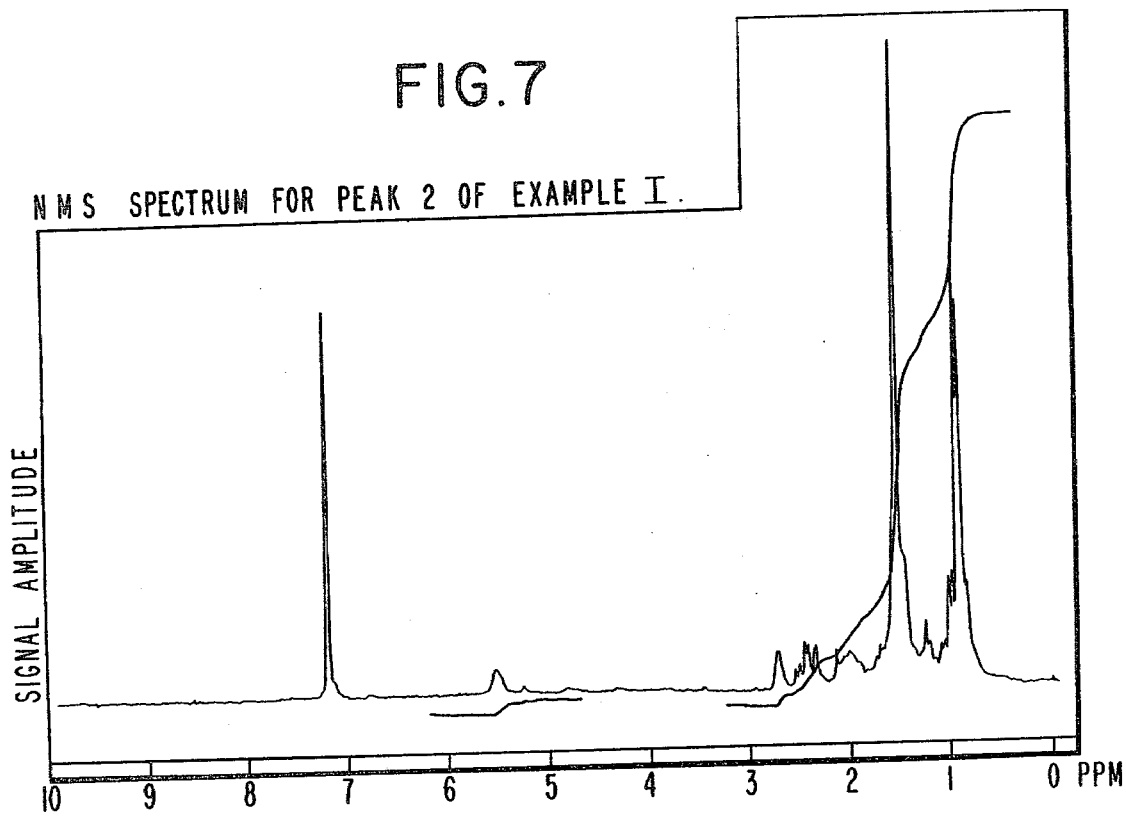
FIG. 7
NMS SPECTRUM FOR PEAK 2 OF EXAMPLE I.
FIG. 8
EXAMPLE I
PEAK 3
1-BUTYROYL-2,6,6 TRIMETHYL CYCLONE X-1-ONE
MASS SPECTRUM
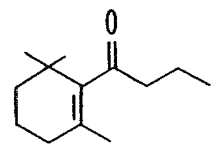
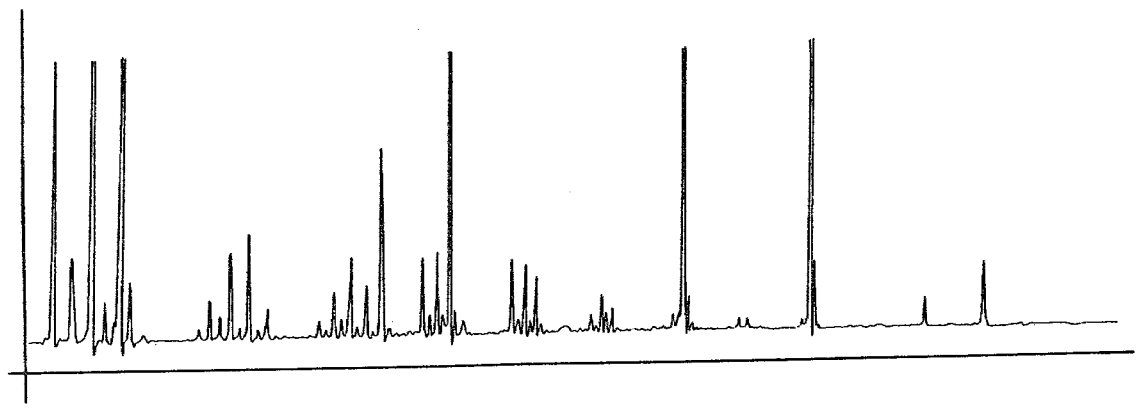

I.R. SPECTRUM FOR EXAMPLE I, PEAK 3.

NMR SPECTRUM FOR PEAK 3 OF EXAMPLE I

EXAMPLE II(B)
GLC PROFILE
(REACTION USING Pd/BaSO₄ CATALYST).

EXAMPLE II(B)
PEAK 1
1-BUTYPYL-2,6,6 TRIMETHYL-CYCLOHEX-2-ENE
MASS SPECTRUM

I.R. SPECTRUM FOR EXAMPLE II(B), PEAK I.

NMR SPECTRUM FOR EXAMPLE II(B) PEAK I.

EXAMPLE II(B)
PEAK 2
1-BUTYRIYL-2,6,6 TRIMETHYL CYCLOHEXA-1-ENE
MASS SPECTRUM

I.R. SPECTRUM FOR EXAMPLE II(B), PEAK 2

EXAMPLE II(B)
PEAK 3
MASS SPECTRUM

I.R. SPECTRUM FOR EXAMPLE II(B).

NMR SPECTRUM FOR EXAMPLE XVII.

PROCESS FOR HYDROGENATION OF 2,6,6-TRIMETHYL CYCLOHEXENE DERIVATIVES AND ORGANOLEPTIC USES OF SAID PRODUCTS

This is a divisional of application Ser. No. 969,852, filed Dec. 15, 1978, now U.S. Pat. No. 4,292,447, issued Sept. 29, 1981.

BACKGROUND OF THE INVENTION

The present invention provides butenoyl and butanoyl cyclohexane and cyclohexene compounds defined by the generic structure:

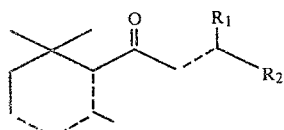
(II)

wherein in the cyclohexyl group one of the dashed lines is a double bond and the other two dashed lines are single bonds or each of the three dashed lines are single bonds; in the butanoyl side chain, the dashed line is a single bond or a double bond and wherein one of $R_1$ or $R_2$ is methyl and the other of $R_1$ or $R_2$ is hydrogen. These compounds are prepared by a straightforward economical process also covered by this invention, which process involves the treatment with hydrogen of a compound having the generic structure:

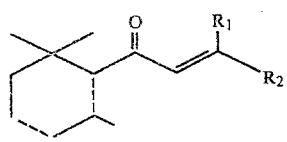
(I)

wherein one of the dashed lines or both of the dashed lines are carbon-carbon double bonds and wherein one of $R_1$ or $R_2$ is hydrogen and the other of $R_1$ or $R_2$ is methyl. The compounds are prepared by means of the following reaction sequence:

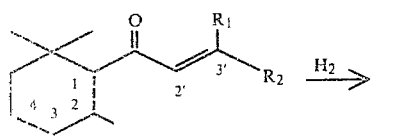

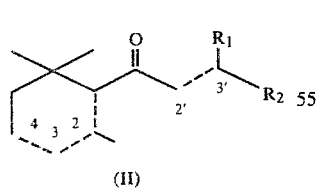

wherein the cyclohexyl moiety of structure (II) contains a maximum of two double bonds only when the cyclohexyl moiety of structure (I) contains two double bonds.

The present invention also provides for the utilization of the compounds produced by our invention and mixtures produced by the process of our invention which contain the compounds having the chemical structures:

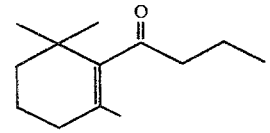

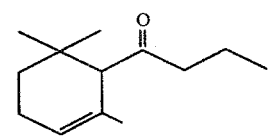

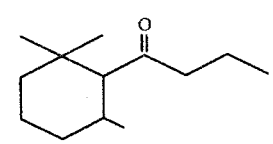

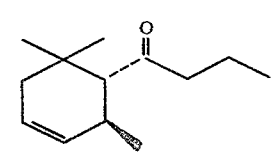

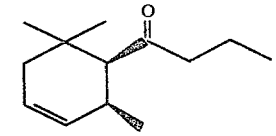

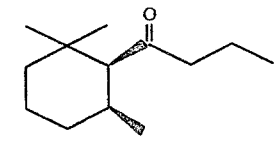

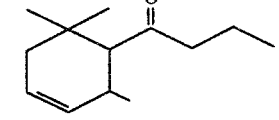

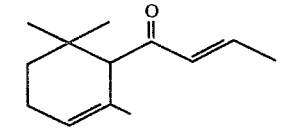

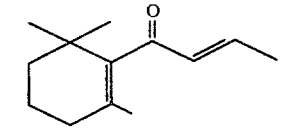

and

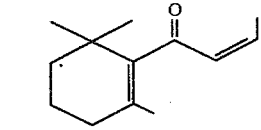

or defined by the generic structure:

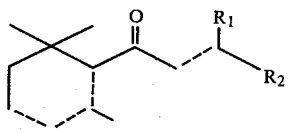 (II)

wherein R₁, R₂ and the dashed lines are as above defined, for their organoleptic properties in perfumes, perfumed articles, foodstuffs, foodstuff flavoring compositions, chewing gums, toothpastes, medicinal products, tobaccos, tobacco flavoring compositions, substitute tobaccos and substitute tobacco flavoring compositions.

In the perfumery art there is considerable need for constituents having floral, rose-like, sweet, dry fruity, tobacco-like aromas with heavy fruity (berry), hay-like and slightly camphoraceous undertones. Sweet, full ripe raspberry-like, fruity, grape juice-like, apple juice-like, dried-fruit-like damascenone-like, floral, woody, aroma and flavor characteristics are desirable in many fruit flavors, particularly raspberry flavors, tangerine flavors, grape flavors and apple flavors. Wheat, fruity, hay-like, minty/spicey and woody aromas both prior to and on smoking in the mainstream and in the sidestream are desirable in smoking tobacco flavoring compositions and substitute smoking tobacco flavoring compositions.

Specifically described herein are materials having such an organoleptic profile but which do not discolor with age. Such materials have a wide utilization in the presence of perfume compounds and in foodstuff flavor and tobacco flavoring compounds. A limited amount of such materials that give rise to one or more of these properties individually, is available from natural sources but the natural materials are subject to wide variations in quality, are expensive and are often in critically short supply.

In addition, there is a continuing search for flavor compositions which can vary, fortify, modify, enhance, augment or otherwise improve the flavor and/or aroma of foodstuffs, medicinal products, toothpastes and chewing gums. To be satisfactory, such compositions should be stable, non-toxic and blendable with other ingredients to provide their own unique flavor and aroma nuances without detracting from the contributions of the co-ingredients. Preferably such compositions should be naturally occurring or present in natural foodstuffs so that their ingestible safety can be readily recognized. These materials should be capable of being synthesized in a simple and economical manner. The need for safe flavors in the berry fruit flavor area, especially the raspberry area, the grape flavor area and the apple flavor area is well known particularly in the fruit juice, ice cream and yogurt flavor areas. More specifically, there is a need for the development of non-toxic materials which can replace natural materials not readily available having sweet, full ripe, raspberry-like, fruity, grape juice-like, apple juice-like, dried-fruit-like, floral and woody aroma and flavor characteristics.

The instant invention provides the foregoing which the prior art has heretofore failed to provide. Furthermore, nothing in the prior art shows the unexpected, unobvious and advantageous value of carrying out a hydrogenation process on compounds having the generic structure:

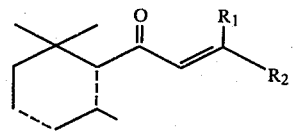 (I)

wherein at least one of the dashed lines of structure (I) is a carbon-carbon double bond and the other of the dashed lines is a carbon-carbon single bond and one of R₁ or R₂ is hydrogen and the other of R₁ or R₂ is methyl, to provide compounds having the generic structure:

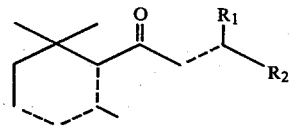 (II)

wherein at least two of the dashed lines in the cyclohexane moiety of structure II is a carbon-carbon single bond and the other of the dashed lines in the cyclohexane moiety of structure II is either a carbon-carbon single bond or a carbon-carbon bond; and wherein the dashed line in a butanoyl moiety of structure II is a carbon-carbon single bond or a carbon-carbon double bond and one of the moieties R₁ or R₂ is hydrogen and the other of the moieties R₁ or R₂ is methyl.

Described in a prior art are mixtures presumed to be predominantly cis,trans-delta-damascone with minor amounts of trans,trans-delta-damascone (Ayyar, Cookson and Kagi, J. Chem. Soc., Perkin Trans. 1, 1975 (17) 1727–36 [title: "Synthesis of Delta-Damascone [trans-1-(2,6,6-trimethylcyclohex-3-enyl)but-2-en-1one] and Beta-Damascenone [trans-1-(2,6,6-trimethylcyclohexa-1,3-dienyl)but-2-en-1-one]"]. The reaction sequence of the Ayyar synthesis, however, does not concern the step of hydrogenation and is as follows:

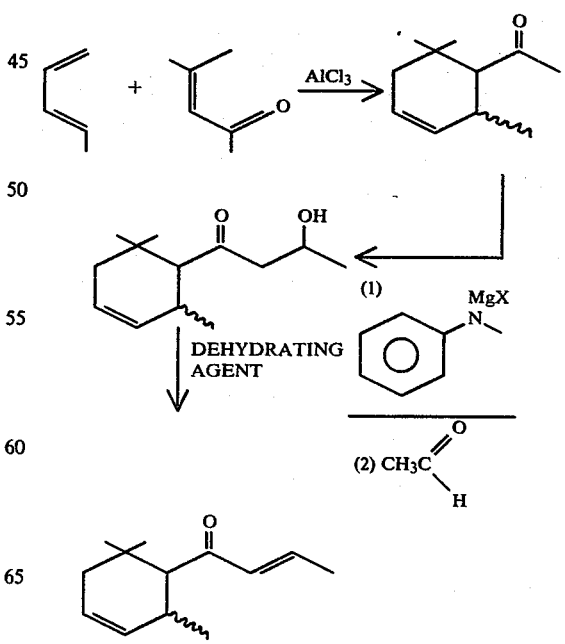

wherein the wavy line is representative of a "cis" or "trans" configuration of the methyl moiety with respect to the acetyl or crotonoyl moiety, both of which are bonded to the cyclohexenyl moiety, the "cis" isomer presumably being the major isomer and the "trans" isomer presumably being the minor isomer in this reaction sequence.

In U.S. Pat. No. 3,956,392 at column 7 and 8 it is indicated that trans,e-1-crotonyl-2,2,6-trimethylcyclohexane (totally saturated insofar as the ring moiety is concerned) has unexpected, unobvious properties over cis,-e-1-crotonyl-2,2,6-trimethylcyclohexane; e-beta-damascenone and e-beta-damascone. The properties of the compound of U.S. Pat. No. 3,956,392 are different in kind rather than degree from the organoleptic properties of the mixtures produced according to the hydrogenation processes of our invention.

Swiss Pat. No. 537,352 issued on July 13, 1973 discloses 1(2-butenoyl)cyclohexenes having the structure:

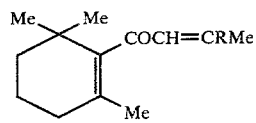

(wherein R may be hydrogen) and this Swiss Patent is abstracted in Chem. Abstracts 79:104808s.

The article, "Structure et synthese de la damascenone (trimethyl-2,6,6-trans-crotonoyl-1-cyclohexadiene-1,3), constituant odorant de L'essence de rose bulgare (Rosa damascena Mill.)" by E. Demole, P. Enggist, U. Sauberli and M. Stoll (referred to herein as Demole, et. al.) discloses the presence of 2,6,6-trimethyl-1(trans-crotonyl)-1,3-cyclohexadiene as an "odorous constituent of Bulgarian rose oil". In addition, the Demole et. al. article discloses that dihydro-alpha-damascone results from the "catalytic hydrogenation" of "dehydro-alpha-damascone" produced via "dehydro-iso-ionol". On page 550 of the Demole article, 1,5,5(trimethylbutyne-2-oyl)-6-cyclohexene is indicated to be treated with a Lindlar catalyst of the type used in the instant case thereby producing a mixture containing 4:1 (mole ratio) of alpha-cis-damascone and dihydro-alpha-damascone. The use of such Lindlar catalyst as is set forth in the Demole et. al. reference is well known in the art as is seen in Canadian Pat. No. 1,022,187 wherein citral, 3,7-dimethyl-2,6-octadienal is converted to citronellal with yields in excess of 95% by the use of a palladium catalyst and hydrogen gas in an alkaline alcoholic reaction medium. It is indicated that the palladium can be used in any form in Canadian Pat. No. 1,022,187 but preferably that the palladium is supported on a "suitable inert carrier such as charcoal, alumina, barium carbonate, aluminum sulfate, carbon or silica gel".

Nothing in Canadian Pat. No. 1,022,187 or in the Demole et. al. article implied that the catalyst of the instant case can be used in such a manner in conjunction with the hydrogenation of compounds having the generic structure:

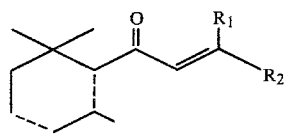

wherein the dashed lines and $R_1$ and $R_2$ are as defined above, whereby compounds having the generic structure:

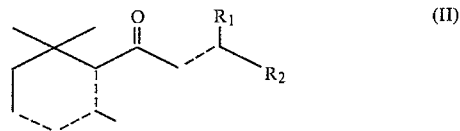

in admixture in the proportions indicated can be produced.

In addition, none of the foregoing references discloses the treatment with hydrogen of any one of the genus of compounds having the structure:

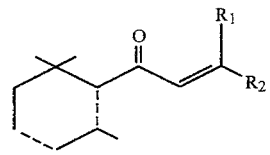

wherein at least one of the dashed lines is a carbon-carbon double bond and the other of the dashed lines is a carbon-carbon single bond and wherein one of $R_1$ or $R_2$ is hydrogen and the other of $R_1$ or $R_2$ is methyl.

BRIEF DESCRIPTION OF THE DRAWINGS

FIG. 1 is the GLC profile for the reaction product of Example I wherein the peaks represent the indicated structures.

FIG. 2 is the mass spectrum for for peak 1 of the GLC profile of the reaction product produced according to Example I and is substantially 1-butyryl-2,2,6-trimethylcyclohexane.

FIG. 7 is the NMR spectrum for peak 2 of the GLC profile of the reaction product produced according to Example I.

FIG. 8 is the mass spectrum for peak 3 of the GLC profile of the reaction product produced according to Example I, substantially 1-butyryl-2,6,6-trimethylcyclohex-1-ene.

THE INVENTION

Figure 3:
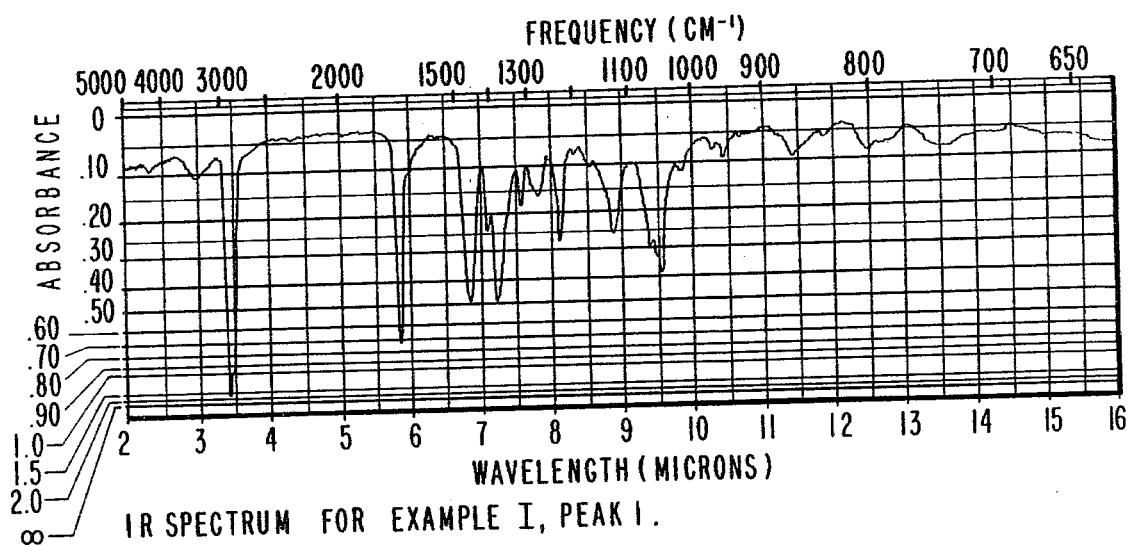
FIG. 3 is the infrared spectrum for peak 1 of the GLC profile of the reaction product produced according to Example I.

The present invention provides an economical, efficient process for synthesizing compounds having the generic structure:

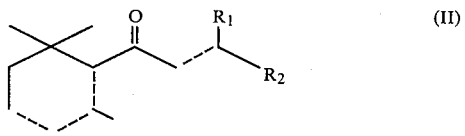

wherein in the cyclohexyl moiety of structure II, at least two of the dashed lines are carbon-carbon single bonds and the other of the dashed lines is either a carbon-carbon double bond or a carbon-carbon single bond; and wherein in the butanoyl side chain, the dashed line is either a carbon-carbon single bond or a carbon-carbon double bond; and wherein one of $R_1$ or $R_2$ is hydrogen and the other of $R_1$ or $R_2$ is methyl. Examples of structures of compounds represented by the generic structure:

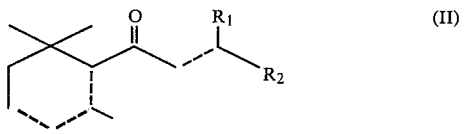

are as follows:

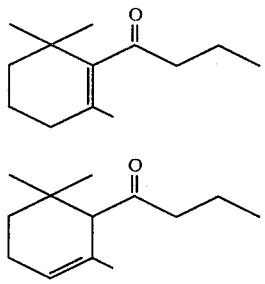

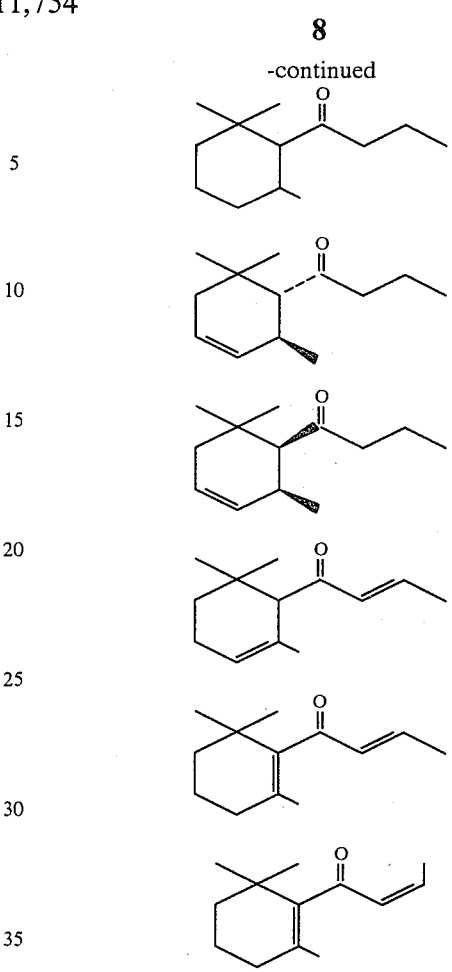

The butanoyl trimethylcyclohexane derivatives of our invention as well as mixtures thereof produced according to the hydrogenation process of our invention are capable of augmenting or enhancing sweet, damascenone-like, full ripe raspberry-like, fruity, grape juice-like, apple juice-like, dried-fruit-like and woody aromas and flavors particularly in raspberry- grape- tangerine- and apple-flavored foodstuffs.

The butenoyl and butanoyl cyclohexane and cyclohexane compounds and mixtures thereof of our invention are also capable of augmenting, enhancing or modifying the odor characteristics of perfume compositions, colognes and perfumed articles by imparting thereto or augmenting or enhancing the floral, rose-like, sweet, dried fruit, tobacco-like fragrance notes thus fulfilling a need in the field of perfumery.

In smoking tobacco and smoking tobacco flavoring compositions and in substitute smoking tobacco and in substitute smoking tobacco flavoring compositions the compounds produced according to the novel process of our invention, the butenoyl and/or butanoyl cyclohexane and cyclohexane compounds augment and enhance the sweet, fruity, hay-like, minty/spicey, hay-tobacco-like, hay-tea-like aroma and taste notes prior to and on smoking in the mainstream and in the sidestream.

The butenoyl and/or butanoyl cyclohexane and cyclohexene compounds and mixtures thereof of our invention are produced by, in general, reacting with hydrogen a compound or mixture of compounds defined according to the structure:

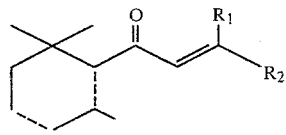

(I)

where at least one of the dashed lines in the cyclohexane moiety of structure I is a carbon-carbon double bond and the other of the dashed lines is a carbon-carbon single bond and one of $R_1$ or $R_2$ is hydrogen and the other of $R_1$ or $R_2$ is methyl according to the following reaction scheme:

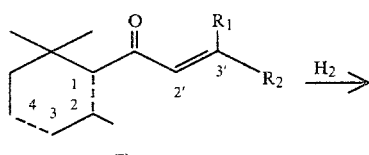

(I)

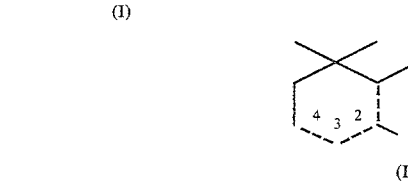

(II)

More specifically, when carbon-carbon double bonds exist at the "1" and "3" positions of compound I, hydrogenation of compound I in the presence of a supported palladium catalyst (palladium-on-calcium carbonate or palladium-on-barium sulfate) and a solvent such as ethyl acetate will give rise to a mixture of compounds containing a compound having unsaturation at the $\Delta^{2,3}$ position or complete saturation in the ring moiety. It is preferable to also include a catalyst "deactivator" with the supported palladium catalyst such as quinoline. In addition, compounds in the resulting mixtures will be produced wherein there is a saturation at the $\Delta^{2,3}$ position of the side chain or there is unsaturation at that position. Even more specifically, when a palladium-on-calcium carbonate catalyst is used in the hydrogenation of a compound having the structure:

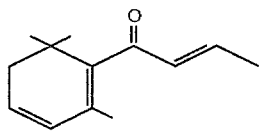

the following reaction takes place:

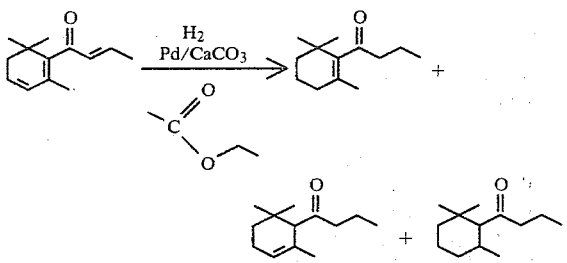

On the other hand, when the compound reacted is, for example, cis, trans-delta-damascone (as described and synthesized by Ayyar, et. al. cited supra) the reaction sequence taking place is as follows:

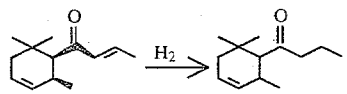

When the catalyst used is palladium supported on barium sulfate, and the reactant has the structure:

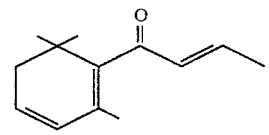

the reaction taking place is as follows:

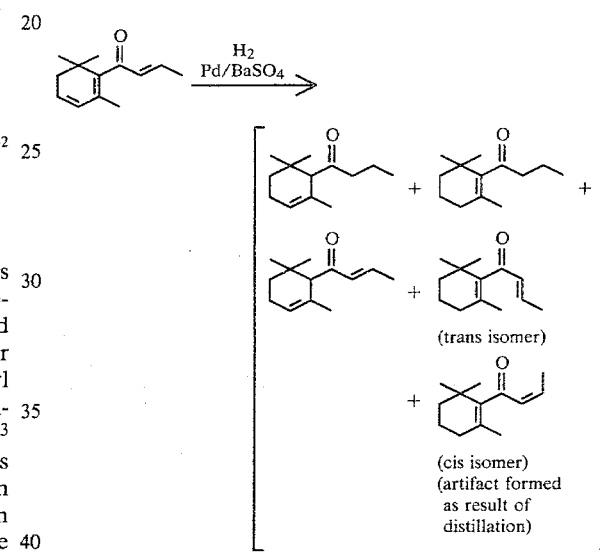

(trans isomer)

(cis isomer)
(artifact formed as result of distillation)

The amount of palladium in the catalyst composition may vary from 2% up to about 10% with the support being either calcium carbonate or barium sulfate. The preferable quantity of palladium in the catalyst is about 5%. The ratio of catalyst (including the support) to reactant having the generic structure:

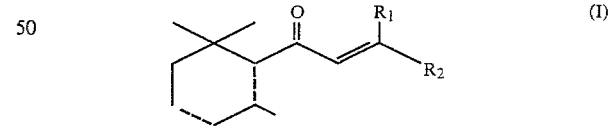

(I)

for example, compounds such as beta damascenone having the structure:

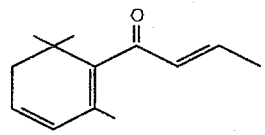

may vary from 0.05:1 up to 0.5:1 with a preferred ratio of catalyst:reactant being about 0.1:1 (weight:weight). When using a palladium-on-calcium carbonate catalyst, it is preferred that a solvent also be used in the reaction with hydrogen and such solvent is preferably an inert solvent such as an inert ester, for example, ethyl acetate or n-propyl acetate or n-butyl acetate or ethyl n-propionate or n-propyl-n-propionate or n-butyl n-propionate or diethyl phthalate. The concentration of reactant such as beta damascenone in solvent may vary from about 1:10 up to about 1:50 with a concentration of reactant in solvent of about 5% being preferable.

The hydrogenation reaction preferably takes place at "ambient" conditions, i.e., room temperature, 20°–30° C. and one atmosphere pressure. However, higher pressures up to about 100 atmospheres and higher temperatures up to about 50° C. may be used without detrimentally affecting the yield of desirable product produced. Indeed, in many instances higher temperatures of reaction give rise to shorter times of reaction and use of shorter times of reaction is advantageous from an economical standpoint.

Examples of the products produced according to the process of our invention and their organoleptic properties are as follows:

TABLE I

| Structure of Products either taken alone or in admixture | Perfumery Properties | Food Flavor Affecting Properties | Tobacco Flavor Affecting Properties |
|---|---|---|---|
| 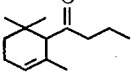 | At 1% in dipropylene glycol, a sweet, dry, fruity, floral aroma with hay tobacco nuances. | A sweet, damascenone-like, full, ripe, raspberry-like, fruity, grape juice-like, aroma and flavor character at 1 ppm. | A fruity, berry-like, damascenone-like, hay tea-like aroma with sweet, floral, fruity nuances prior to and on smoking in the mainstream and the sidestream and also resulting from treatment of the filter (20 microliter filter or 200 ppm.). |
| 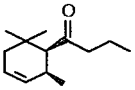 (Mixture containing 83% cis,trans and 17% trans,trans) | | A sweet, fruity, raspberry-like, grape juice-like, apple juice-like, dried-fruit-like, damascenone aroma and flavor characteristics with a cooling effect at 1 ppm. | |
| 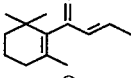 | A floral (rose) fruity (prune, berry-like) aroma. | A damascenone-like, floral woody and fruity aroma and flavor characteristics 2.0 ppm. | |
| 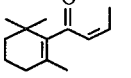 | A burnt, rosey aroma with weak floral nuances. | A fruity, woody, floral damascenone-like aroma and flavor characteristics at 2 ppm. | |
| Mixture of Compounds having the Structures | Perfumery Properties | Food Flavor Affecting Properties | Tobacco Flavor Affecting Properties |
| 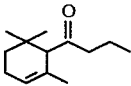 + 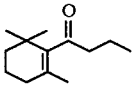 + 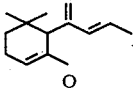 + 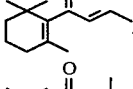 (mixture) (artifact found as result of distillation) | A floral, rose-like aroma with heavy fruity (berry) undertones; also hay and slightly camphoraceous nuances. | A sweet, fruity, raspberry-like, rosebuds-like aroma with sweet, fruity, raspberry flavor characteristics with a rosebuds nuance at 0.005 ppm. | A sweet, fruity, hay, minty/spicey, woody, aroma and flavor profile both prior to and on smoking in the mainstream and in the sidestream. |

When the butenoyl and butanoyl cyclohexane and cyclohexene compounds and mixtures thereof of our invention are used as food flavor adjuvants, the nature of the co-ingredients included with the butenoyl and butanoyl cyclohexane and cyclohexene compounds and mixtures thereof of our invention used in formulating the product composition will also serve to alter, modify, augment or enhance the organoleptic characteristics of the ultimate foodstuff treated therewith.

As used herein in regard to flavors, the terms "alter", "modify" and "augment" in their various forms mean supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids while are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chickle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates the butenoyl and butanoyl cyclohexane and cyclohexene compounds and mixtures thereof of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and/or taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chloride, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and cis and trans 2-methyl-3-pentenoic acids; ketones and aldehydes, e.g., acetaldehyde, acetophenone, acetone, acetyl methyl carbinol, acrolein, n-butanal, crotonal diacetyl, 2-methyl butanal, beta, beta-dimethyl-acrolein, methyl-n-amyl ketone, 2-hexanal, 2-hexenal, iso-pentanal, hydrocinnamic aldehyde cis-3-hexenal, 2-heptenal, n-nonyl aldehyde, 4-(p-hydroxyphenyl)-2-butanone, alpha-ionone, beta-ionone, methyl-3-butanone, benzaldehyde, beta-damascone, beta-damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanol; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, iso-amyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2-5-dimethylpyrazine, 2-6-dimethylpryazine, 3-ethyl- 2,5-dimethyl-pryazine, 2-ethyl-3,5,6-trimethylpryazine, 3-isoamyl-2,5-dimethyl-pyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpryazine; essential oils, such as jasmine absolute, cassia oil, cinnamon bark oil, rose absolute, orris absolute, lemon essential oil, Bulgarian rose, yara yara and vanilla; lactones such as delta nonalactone, gamma, nonalactone, delta dodecalactone, gamma dodecalactone, sulfides, e.g., methyl sulfide and other materials such as maltol, acetoin and acetals (e.g., 1,1-diethoxyethane, 1,1-dimethoxyethane and dimethoxymethane.

The specific flavoring adjuvant selected for use may be either solid or liquid depending upon the desired physical form of the ultimate product, i.e., foodstuff, whether simulated or natural, and should, in any event, (i) be organoleptically compatible with the butenoyl and butanoyl cyclohexane and cyclohexane compounds and mixtures thereof of our invention by not covering or spoiling the organoleptic properties (aroma and/or taste) thereof; (ii) be non-reactive with the butenoyl and butanoyl cyclohexane and cyclohexene compounds and mixtures thereof of our invention and (iii) be capable of providing an environment in which the butenoyl and butanoyl cyclohexane and cyclohexene compounds and mixtures thereof of our invention can be dispersed or admixed to provide a homogeneous medium. In addition, selected of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the butenoyl and/or butanoyl cyclohexane and cyclohexane compounds and/or mixtures thereof of our invention employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of butenoyl and/or butanoyl cyclohexane and cyclohexene compounds and/or mixtures thereof will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of butenoyl and butanoyl cyclohexane and cyclohexene compounds and mixtures thereof ranging from a small but effective amount, e.g., 0.002 ppm up to about 100 ppm based on total composition are suitable. Concentrations in excess of the maximum quantity stated are not normally recommended, since they fail to provide commensurate enhancement of organoleptic properties. In those instances, wherein the butenoyl and butanoyl cyclohexane and cyclohexene compounds and mixtures thereof of our invention are added to the foodstuff as an integral component of a flavoring composition, it is, of course, essential that the total quantity of flavoring composition employed by sufficient to yield an effective concentration of butenoyl and/or butanoyl cyclohexane and cyclohexene compounds or mixtures thereof in the foodstuff product.

Food flavoring compositions prepared in accordance with the present invention preferably contain the butenoyl and/or butanoyl cyclohexane and cyclohexene compounds or mixtures thereof of our invention in concentrations ranging from about 0.1% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the butenoyl and/or butanoyl cyclohexane and cyclohexene compounds or mixtures thereof of our invention with, for example, gum arabic, gum tragacanth, carrageenan and the like, and thereafter spray-drying the resultant mixture whereby to obtain the particulate solid product. Pre-prepared flavor mixes in powder form, e.g., fruit-flavored powder mixes are obtained by mixing the dried solid components, e.g., starch, sugar and the like and the butenoyl and/or butanoyl cyclohexane and cyclohexene compounds or mixtures thereof of our invention in a dry blender until the requisite degree of uniformity is achieved.

It is presently preferred to combine with the butenoyl and/or butanoyl cyclohexane and cyclohexene compounds or mixtures thereof of our invention, the following adjuvants:

p-Hydroxybenzyl acetone;
Geraniol;
Cassia Oil;
Acetaldehyde;
Maltol;
Ethyl Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;

Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
Beta-Damascone (1-crotonyl-2,6,6-trimethyl-cyclohex-1-ene);
Beta-Damascenone (1-crotonyl-2,6,6-trimethyl-cyclohexa-1,3-diene);
Beta-cyclohomocitral (2,6,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene.

The butenoyl and/or butanoyl cyclohexane and cyclohexene compounds or mixtures thereof and one or more auxiliary perfume ingredients, including, for example, alcohols, aldehydes, ketones other than the butenoyl and/or butanoyl cyclohexane and cyclohexene compounds or mixtures thereof of our invention, terpinic hydrocarbons, nitriles, esters, lactones, natural essential oils and synthetic essential oils, may be admixed so that the combined odors of the individual components produce a pleasant and desired fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the overall sensory effect of the perfume composition will be at least the sum total of the effects of each of the ingredients. Thus, the butenoyl and/or butanoyl cyclohexane and cyclohexene compounds or mixtures thereof of our invention can be used to alter, modify to enhance the aroma characteristics of a perfume composition, for example, by utilizing or moderating the olfactory reaction contributed by another ingredient in the composition.

The amount of butenoyl and/or butanoyl cyclohexane and cyclohexene compounds or mixtures thereof of our invention which will be effective in perfume compositions as well as in perfumed articles and colognes depends on many factors, including the other ingredients, their amounts and the effects which are desired. It has been found that perfume compositions containing as little at 0.01% of the butenoyl and/or butanoyl cyclohexane and cyclohexene compounds (or mixtures thereof) or even less (e.g., 0.005%) can be used to impart a sweet, fruity, floral, rosey aroma with hay-tobacco undertones to soaps, anionic, cationic and nonionic detergents, fabric softener articles (such as BOUNCE®, a registered trademark of the Procter & Gamble Company of Cincinnatti, Ohio), cosmetics or other products. The amount employed can range up to 70% of the fragrance components and will depend on considerations of cost, nature of the end product, the effect desired on the finished product and the particular fragrance sought.

The butenoyl and/or butanoyl cyclohexane and cyclohexene compounds or mixtures thereof of our invention are useful (taken alone or together with other ingredients in perfume compositions) as (an) olfactory component(s) in solid and liquid anionic, cationic and nonionic detergents and soaps, space odorants and deodorants, perfumes, colognes, toilet water, bath preparations, such as creams, deodorants, hand lotions and sunscreens; powders, such as talcs, dusting powders, face powders and the like. When used as olfactory components as little as 0.1% of the butenoyl and/or butanoyl cyclohexane and cyclohexene compounds or mixtures thereof of our invention will suffice to impart an intense floral note to rose formulations. Generally, no more than 5% of the butenoyl and/or butanoyl cyclohexane and cyclohexene compounds or mixtures thereof of our invention, based on the ultimate end product, is required in the perfume composition.

In addition, the perfume compositions or fragrance compositions of our invention can contain a vehicle, or carrier for the butenoyl and/or butanoyl cyclohexane and cyclohexene compounds or mixtures thereof of our invention. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin), for example, by means of coacervation.

It will thus be apparent that the butenoyl and/or butanoyl cyclohexane and cyclohexene compounds or mixtures thereof of our invention can be utilized to alter, modify or enhance sensory properties, particularly organoleptic properties, such as flavor(s) and/or fragrance(s) of a wide variety of consumable materials.

Furthermore, the butenoyl and butanoyl cyclohexane and cyclohexene compounds of our invention are capable of supplying and/or potentialting certain flavor and aroma notes usually lacking in many tobacco flavors heretofore provided.

As used herein in regard to tobacco flavors, the terms "alter" and "modify" in their various forms mean "supplying or imparting flavor character or note to otherwise bland tobacco, tobacco substitutes, or tobacco flavor formulations or augmenting the existing flavor characteristic where a natural flavor is deficient in some regard to supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of a tobacco or a tobacco substitute or a tobacco flavor.

Our invention thus provides an organoleptically improved smoking tobacco product and additives therefor, as well as methods of making the same which overcome specific problems heretofore encountered in which specific desired floral, musty, hay- tea-like, sweet and fruity aroma and taste nuances are created or enhanced and may be readily controlled and maintained at the desired uniform level regardless of variations in the smoking tobacco components of the blend.

This invention further provides improved tobacco additives and methods whereby various sweet, fruity, hay-like, minty/spicey, fruity/berry-like, damascenone-like and hay tea-like notes may be imparted to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient at least one of the butenoyl and/or butanoyl cyclohexane and cyclohexene compounds or mixtures thereof of our invention.

In addition to the butenoyl and butanoyl cyclohexane and cyclohexene compounds and mixtures thereof of our invention, other flavoring and aroma additives may be added to the smoking tobacco materials or substitute therefor either separately or in admixture with the butenoyl and/or butanoyl cyclohexane and cyclohexene compounds or mixtures thereof of our invention as follows:

(i) Synthetic Materials

Beta-ethyl-cinnamaldehyde;
Beta-cyclohomocitral;
Eugenol;
Dipentene;
Beta-damascenone;
Alpha-damascone;
Beta-damascone;
Cis,trans-alpha-damascone;
Maltol;
Ethyl Maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho[2,1,b]furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils

Celery seed Oil;
Coffee extract;
Bergamot Oil;
Cocoa extract;
Nutmeg Oil;
Origanum Oil.

An aroma and flavoring concentrate containing one or more of the butenoyl and/or butanoyl cyclohexane and cyclohexene compounds or mixtures thereof of our invention, and, if desired, one or more of the above-indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the butenoyl and/or butanoyl cyclohexane and cyclohexene compounds (or mixtures thereof) to smoking tobacco material is between 250 ppm. and 1,500 ppm. (0.025–0.15%) of the active ingredients to the smoking tobacco material. We have further found that satisfactory results are obtained if the proportion by weight of the sum total of the butenoyl and/or butanoyl cyclohexane and cyclohexene compounds (or mixtures thereof) used to flavoring material is between 2,500 and 15,000 ppm. (0.25%–1.5%).

Any convenient method for incorporating the butenoyl and/or butanoyl cyclohexane and cyclohexene compounds (or mixtures there) in the smoking tobacco product may be employed. Thus, the butenoyl and/or butanoyl cyclohexane and cyclohexene compounds or mixtures thereof of our invention taken alone or taken further together with other flavoring additives as set forth above, may be applied by means of a suitable applicator such as a brush or roller on the paper or leaf wrapper for the smoking product, or it may be applied to the filter by either spraying, dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the butenoyl and/or butanoyl cyclohexane and cyclohexene compounds (or mixtures thereof) of our invention in excess of the amounts or concentrations above-indicated so that when blended with other tobaccos, the final product will have the percentage within the indicated range.

In accordance with one specific example of our invention, an aged, cured and shredded domestic burley tobacco is sprayed with a 20% ethyl alcohol solution of the 1-(2,6,6-trimethyl-2-cyclohexene-1-oyl)-1-butanone produced according to Example II, infra, in an amount to provide a tobacco composition containing 200 ppm. by weight of said 1-(2,6,6-trimethyl-2-cyclohexene-1-oyl)-1-butanone on a dry basis.

Thereafter, the alcohol is removed by evaporation and the tobacco is manufactured into cigarettes by means of the usual techniques. The cigarette when treated as indicated has a desired and pleasing aroma (increased smoke body sensation in the mouth with enhanced tobacco-like notes and pleasant aromatic nuances) which is detectable in the main and sidestreams when the cigarette is smoked. This aroma is described as having a fruity, berry-like, damascenone-like, hay-tea-like aroma with sweet, floral and fruity undertones prior to and on smoking both in the mainstream and the sidestream.

While our invention is particularly useful in the manufacture of smoking tobacco, such as cigarette tobacco, cigar tobacco and pipe tobacco, other tobacco products formed from sheeted tobacco dust or fines may also be used. Likewise, the butenoyl and/or butanoyl cyclohexane and cyclohexene compounds or mixtures thereof of our invention can be incorporated with materials such as filter tip materials, seam paste, packaging materials and the like which are used along with smoking tobacco to form a product adapted for smoking. Furthermore, the butenoyl and/or butanoyl cyclohexane and cyclohexene compounds or mixtures thereof can be added to certain smoking tobacco substitutes of natural or synthetic origin (e.g., dried lettuce leaves) and, accordingly, by the term "tobacco" as used throughout this specification is meant any composition intended for human consumption by smoking, whether composed of tobacco plant parts or substitute materials or both.

The following Examples serve to illustrate out invention. However, our invention is not intended to be limited thereto but is only intended to be limited insofar as the Claims are concerned. All parts and percentages given herein are by weight unless otherwise specified.

EXAMPLE I

Preparation Of Mixture Of Hydrogenated Derivatives Of Beta Damascenone

Reaction

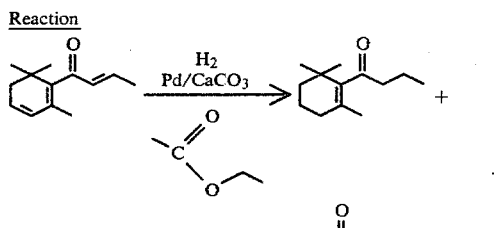

One gram of beta damascenone having the structure:

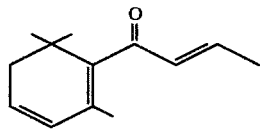

is added to a 50 ml. reaction flask equipped with stirrer, thermometer, gas addition tube along with 20 ml. of ethyl acetate and 100 mg. of "Lindlar" catalyst which is a mixture of 5% palladium-on-calcium carbonate. The resulting mixture is stirred while adding hydrogen at 20°–25° C. and one atmosphere pressure until 120 ml. of hydrogen is absorbed. Preparative GLC (conditions: 10 ft.×⅛ in. 5% carbowax 20 M column programmed at 100°–220° C. at 4° C. per minute) followed by nuclear magnetic resonance analysis, infrared analysis and mass spectral analysis yields the information that the mixture contains 20% of the compound having the structure:

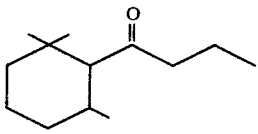

14.7% of the compound having the structure:

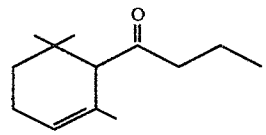

and 59.4% of the compound having the structure:

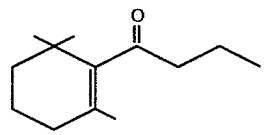

Figure 4:
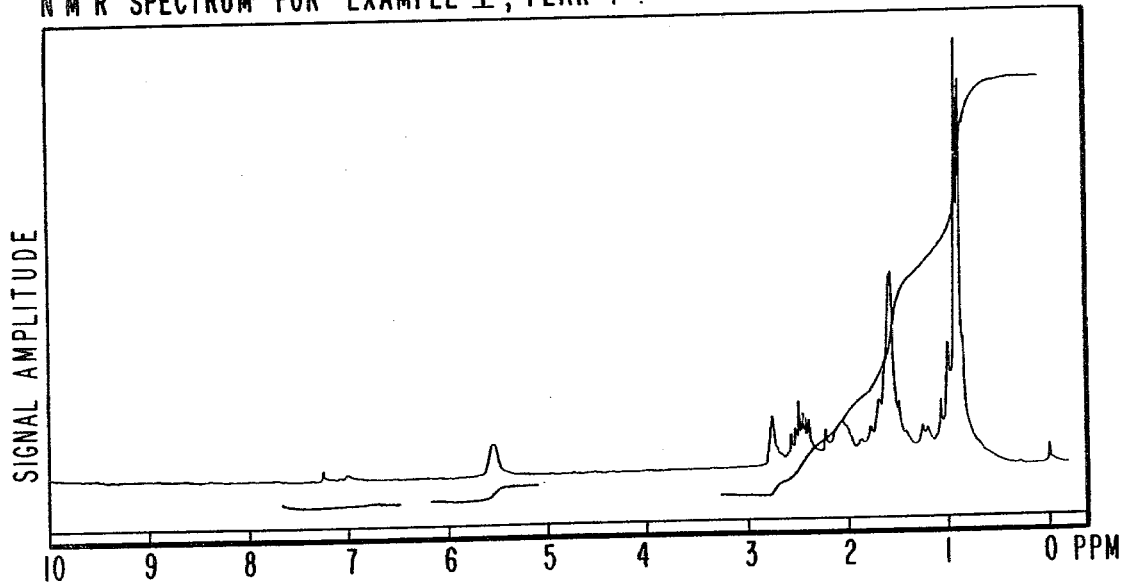
FIG. 4 is the NMR spectrum for peak 1 of the GLC profile of the reaction product produced according to Example I.

The mass spectral analysis for peak 1 of the GLC profile, the compound having the structure:

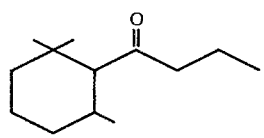

is set forth in FIG. 2. The GLC profile is set forth in FIG. 1. The infrared spectrum for peak 1 is set forth in FIG. 3. The NMR spectrum for peak 1 is set forth in FIG. 4.

Peak 2 is substantially the compound having the structure:

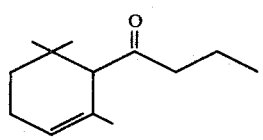

Figures 5, 6:
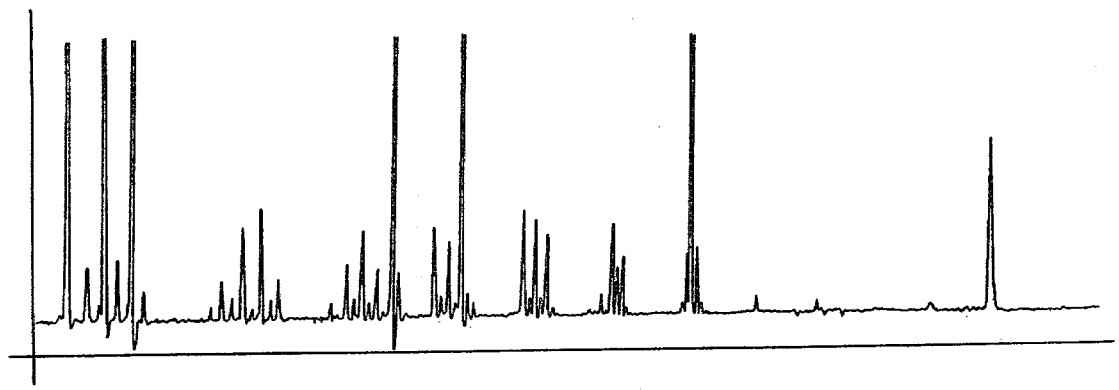
FIG. 5 is the mass spectrum for peak 2 of the GLC profile of the reaction product produced according to Example I which is substantially 1-butyryl-2,2,6-trimethylcyclohex-5-ene.
FIG. 6 is the infrared spectrum for peak 2 of the GLC profile of the reaction product produced according to Example I.

The mass spectrum is set forth in FIG. 5. The infrared spectrum for peak 2 is set forth in FIG. 6. The NMR spectrum for peak 2 is set forth in FIG. 7.

Peak 3 is essentially a compound having the structure:

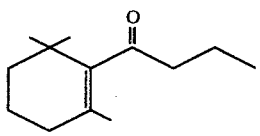

Figure 9:
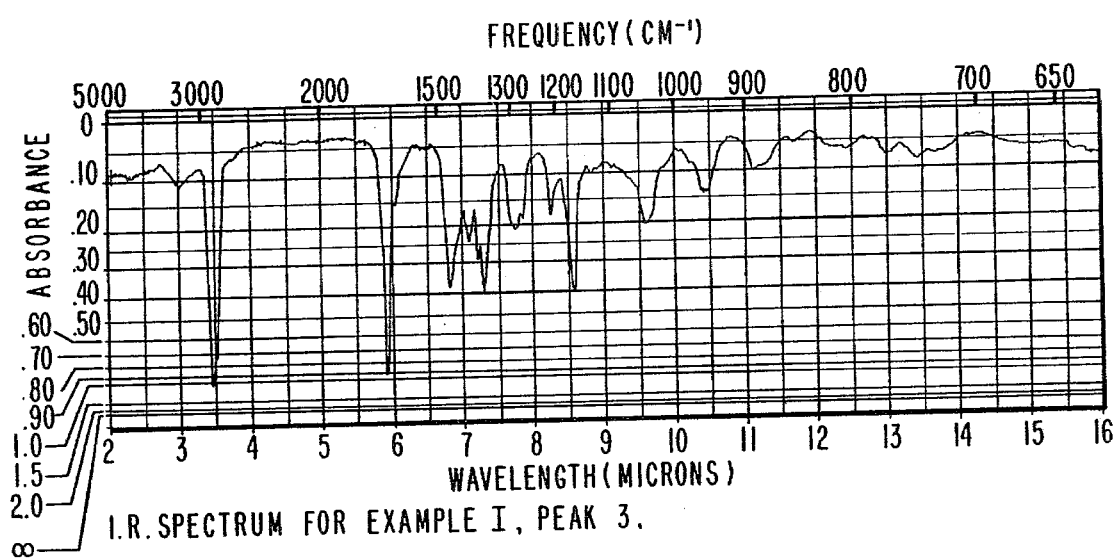
FIG. 9 is the infrared spectrum for peak 3 of the GLC profile of the reaction product produced according to Example I.
Figure 10:
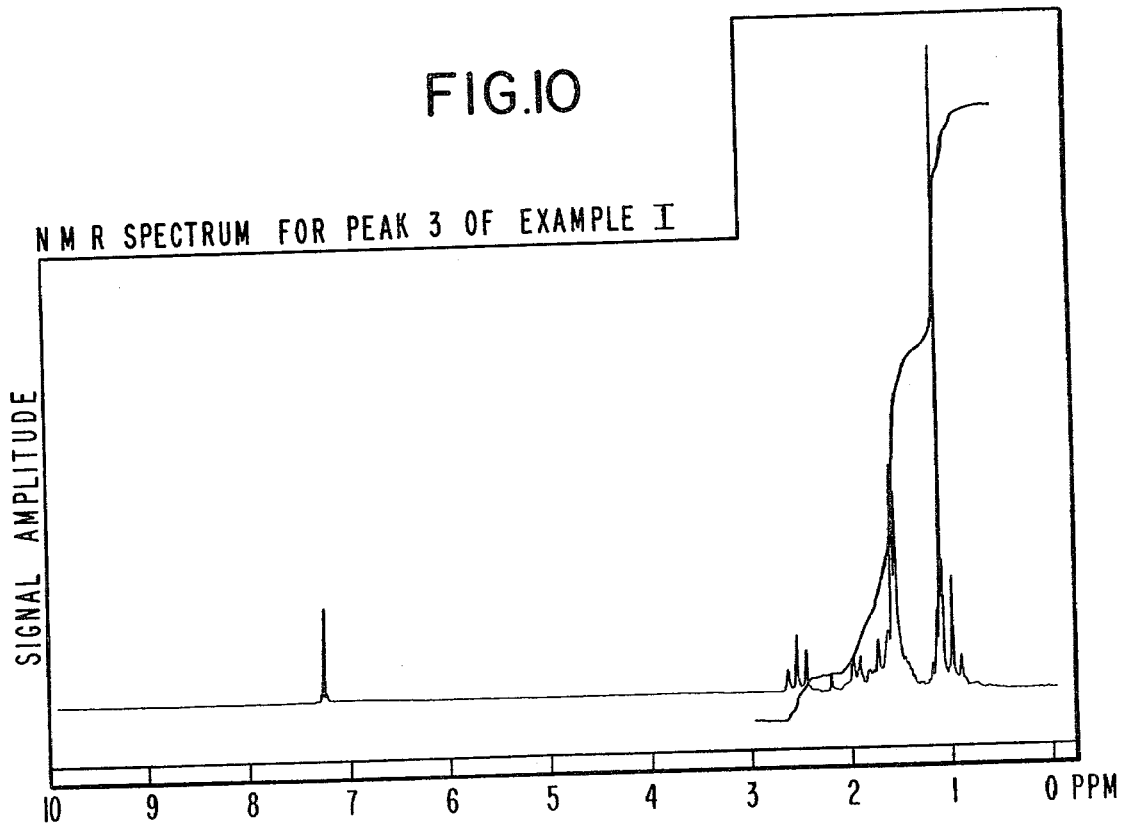
FIG. 10 is the NMR spectrum for peak 3 of the GLC profile of the reaction product produced according to Example I.

The mass spectrum for peak 3 is set forth in FIG. 8. The infrared spectrum for peak 3 is set forth in FIG. 9. The NMR spectrum is set forth in FIG. 10.

The same experiment as set forth above is in carried out wherein ½ gram of beta damascenone is reduced at 20°–25° C. and 1 atmosphere pressure over 100 mg. of Lindlar catalyst in 10 ml. ethyl acetate. 130 ml. of hydrogen are absorbed. The product is then analyzed. The components formed according to GLC mass spectral NMR and IR analyses are as follows:

Peak 1 having the structure:

Peak 2 having the structure:

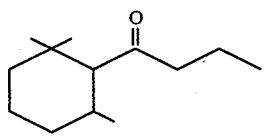

(20% of mixture)

Peak 3 having the structure:

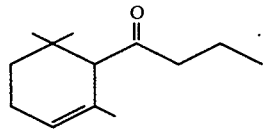

(20% of mixture)

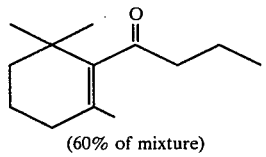

(60% of mixture)

EXAMPLE II

Reaction:

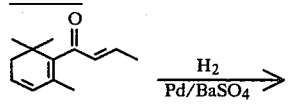

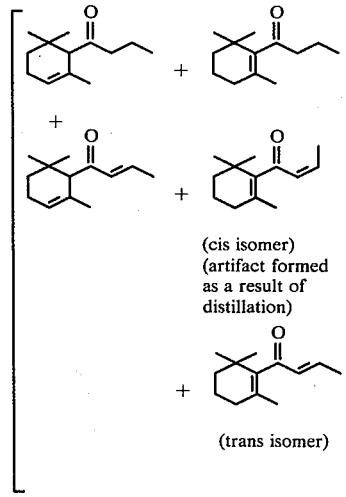

(cis isomer)
(artifact formed as a result of distillation)

(trans isomer)

EXAMPLE II(a)

To a 250 ml. reaction flask is added 10 grams of beta damascenone having the structure:

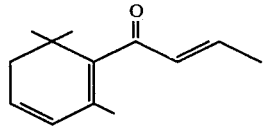

100 ml. ethyl acetate and 0.25 grams of 5% palladium-on-barium sulfate and 0.25 grams of quinoline are then added. The mixture is then hydrogenated at atmospheric pressure and a temperature of 20°–25° C. until an uptake of 1,415 ml. of hydrogen is indicated. GLC analyses are run at about every 100 ml. of hydrogen uptake. The reaction is caused to cease when no more beta damascenone is present. The catalysts are then filtered off and the ethyl acetate evaporated leaving 9.9 grams per product. 150 ml. anhydrous diethyl ether is added and the solution of crude product is washed twice with a 4% aqueous hydrochloric acid solution (20 ml.) and twice with a saturated sodium chloride solution (30 ml.). The ether solution is then dried over anhydrous magnesium sulfate and evaporated leaving 10.0 grams of recovered material. This material is then distilled on a Naster-Faust spinning band column yielding the following fractions:

| Fraction No. | Vapor Temp. (°C.) | Liquid Temp. | Vacuum mm. Hg | Reflux Ratio | Weight of Fraction (gm) |
|---|---|---|---|---|---|
| 1 | 37–44 | 113–115 | .25–.25 | 100:1 | 0.20 |
| 2 | 45 | 119 | 0.25 | 100:1 | 0.40 |
| 3 | 43 | 120 | 0.25 | 100:1 | 0.30 |
| 4 | 80 | 121 | 0.25 | 100:1 | 0.30 |
| 5 | 70 | 119 | 0.4 | 100:1 | 0.05 |
| 6 | 70 | 118 | 0.4 | 100:1 | 0.10 |
| 7 | 60–55 | 122–127 | .3–.3 | 50:1 | 0.10 |
| 8 | 57 | 132 | 0.45 | 50:1 | 0.20 |
| 9 | 64 | 134 | 0.45 | 50:1 | 0.60 |
| 10 | 68 | 136 | 0.45 | 50:1 | 0.80 |
| 11 | 66 | 134 | 0.50 | 50:1 | 0.70 |
| 12 | 62 | 135 | 0.45 | 50:1 | 0.30 |
| 13 | 66 | 143 | 0.60 | 200:1 | 0.50 |
| 14 | 70 | 145 | 0.60 | 200:1 | 0.30 |
| 15 | 70 | 147 | 0.50 | 200:1 | 0.60 |
| 16 | 64 | 150 | 0.50 | 200:1 | 0.40 |
| 17 | 43–52 | 170–180 | .15–.15 | 100:1 | 0.40 |
| 18 | 51 | 195 | 0.15 | 100:1 | 0.20 |
| 19 | 55 | 205 | 0.10 | 100:1 | 0.20 |
| 20 | 53 | 210 | 0.10 | 100:1 | 0.10 |
| 21 | 71 | 235 | .125 | 100:1 | 0.20 |
| 22 | 71 | 235 | .125 | 100:1 | 0.05 |
| 23 | 41–42 | 27–28 | 0.4–0.4 | 100:1 | 0.05 |
| 24 | 42 | 280 | .4 | 5:1 | 0.15 |
| | | | | | 7.2 |

Fractions 2 and 3 are primarily compound having the structure:

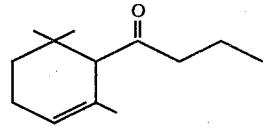

Fractions 7 and 8 are primarily compounds having the structure:

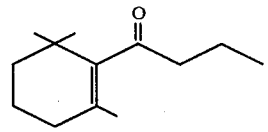

Fractions 12–24 are primarily compounds having the structure:

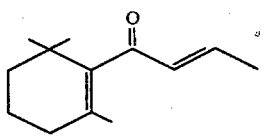

Figure 11:
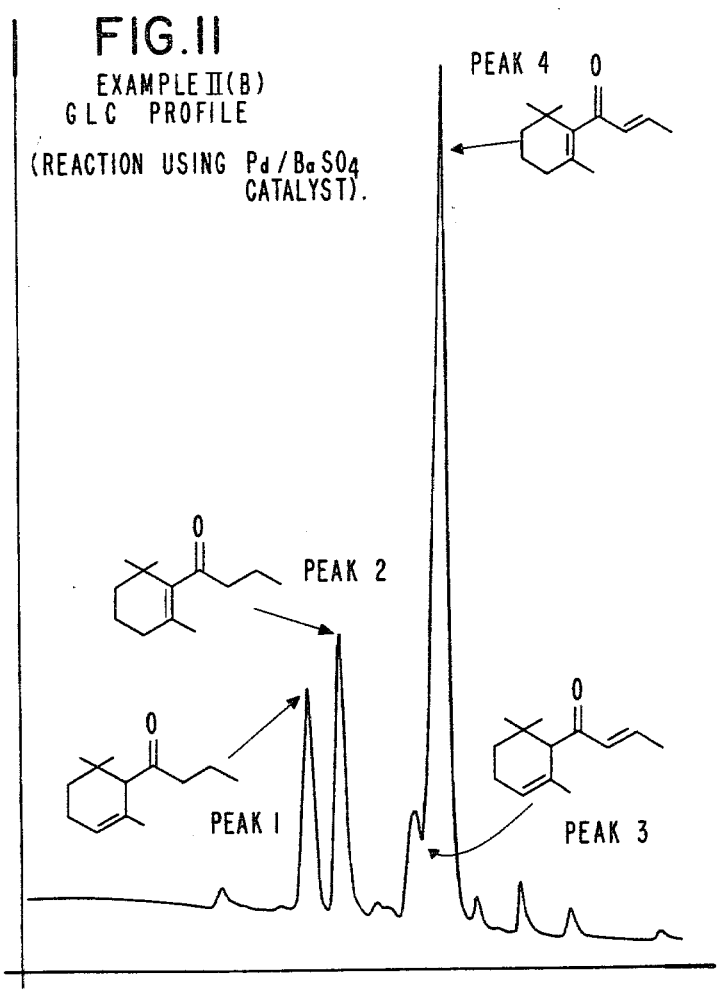
FIG. 11 is the GLC profile for the reaction product produced using a palladium-on-barium sulfate catalyst prepared according to the process of Example II(A). In this GLC profile the several peaks are indicated by structures set forth on the drawing.

FIG. 11 is the GLC profile for the reaction product.

Figure 12:
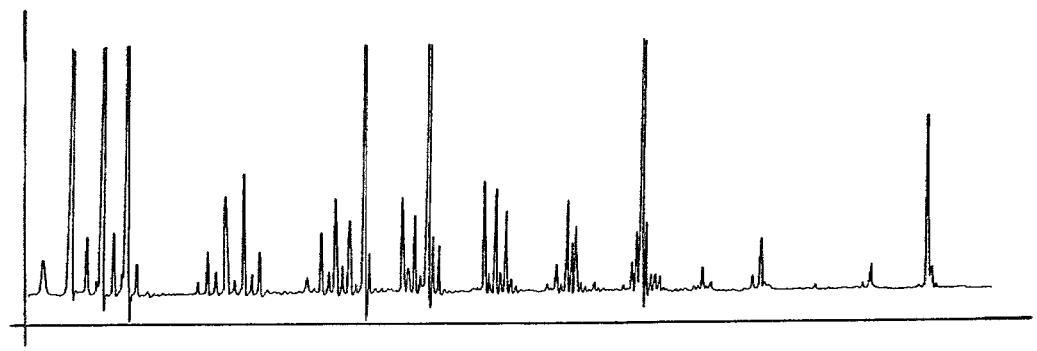
FIG. 12 is the mass spectrum for peak 1 of the GLC profile of the reaction product of Example II(A) which is essentially 1-butyryl-2,6,6-trimethylcyclohex-2-ene.

FIG. 12 is the mass spectrum for peak 1 of the reaction product which is substantially compound having the structure:

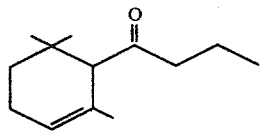

Figure 13:
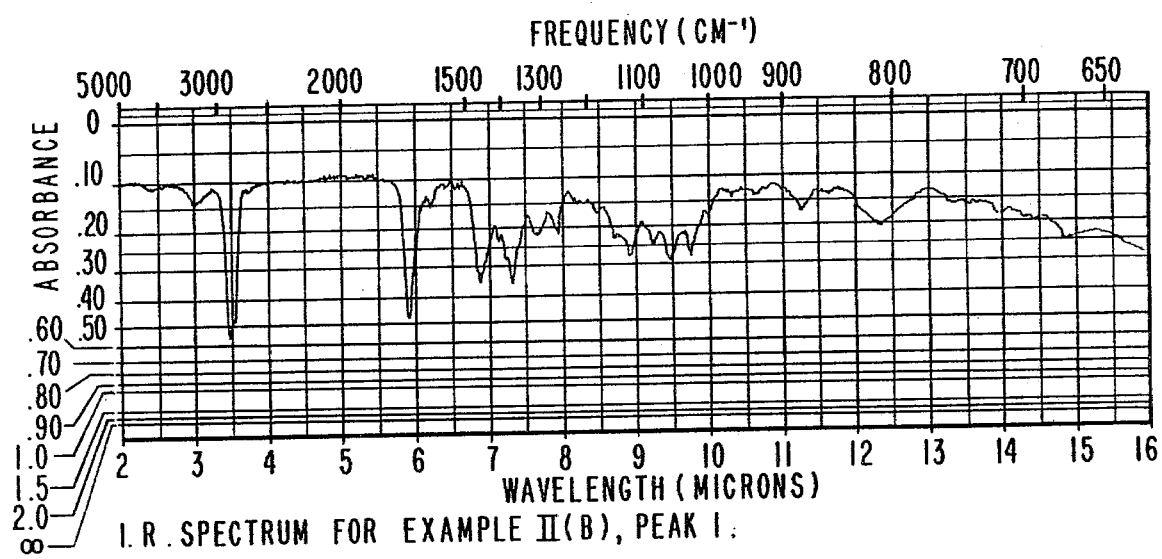
FIG. 13 is the infrared spectrum for peak 1 of the GLC profile of the reaction product produced according to Example II (A).

FIG. 13 is the infrared spectrum for peak 1 of this example.

Figure 14:
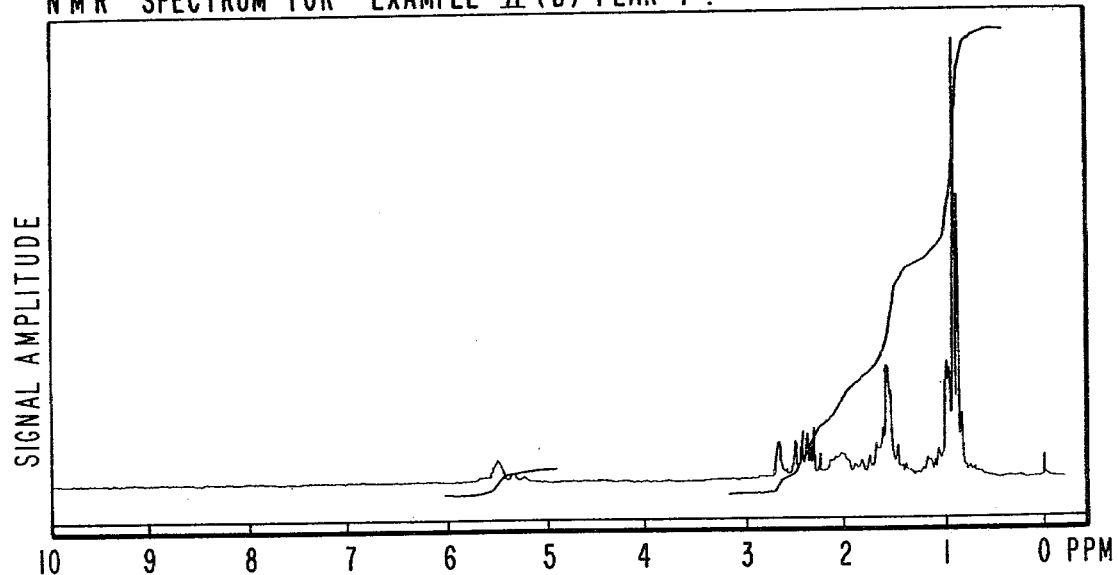
FIG. 14 is the NMR spectrum for peak 1 of the GLC profile of the reaction product produced according to Example II (A).

FIG. 14 is the NMR spectrum for peak 1 of this example.

Figures 15, 16:
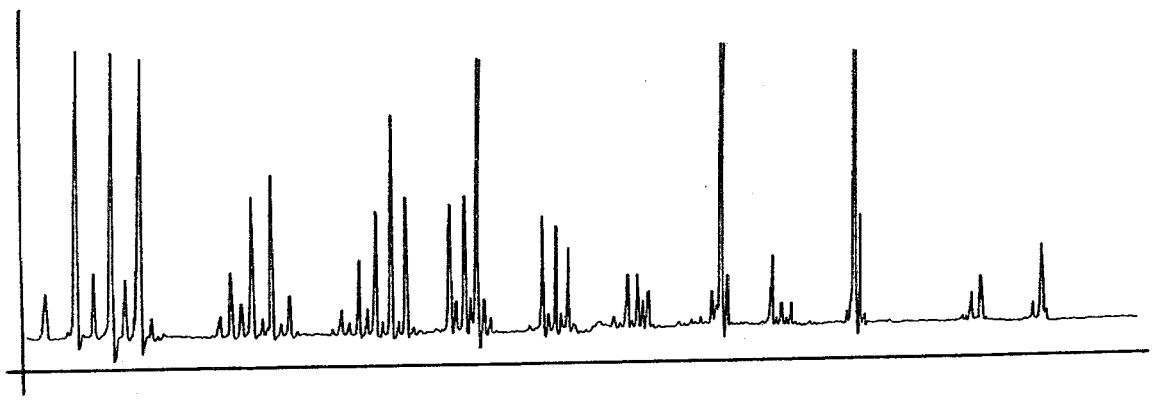
FIG. 15 is the mass spectrum for peak 2 of the GLC profile of the reaction product produced according to Example II (A) which is essentially 1-butyryl-2,6,6-trimethylcyclohex-1-ene.
FIG. 16 is the infrared spectrum for peak 2 of the GLC profile of the reaction product of Example II (A).

FIG. 15 is the mass spectrum for peak 2 of the GLC profile which is substantially compound having the structure:

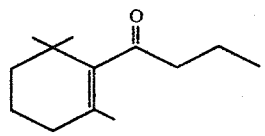

FIG. 16 is the infrared spectrum for peak 2.

Figure 17:
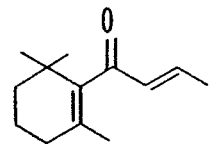
FIG. 17 is the mass spectrum for peak 3 of the GLC profile of the reaction product produced according to Example II(A) which peak is essentially 1(2-butenoyl)-2,6,6-trimethylcyclohex-1-ene.
Figure 17:
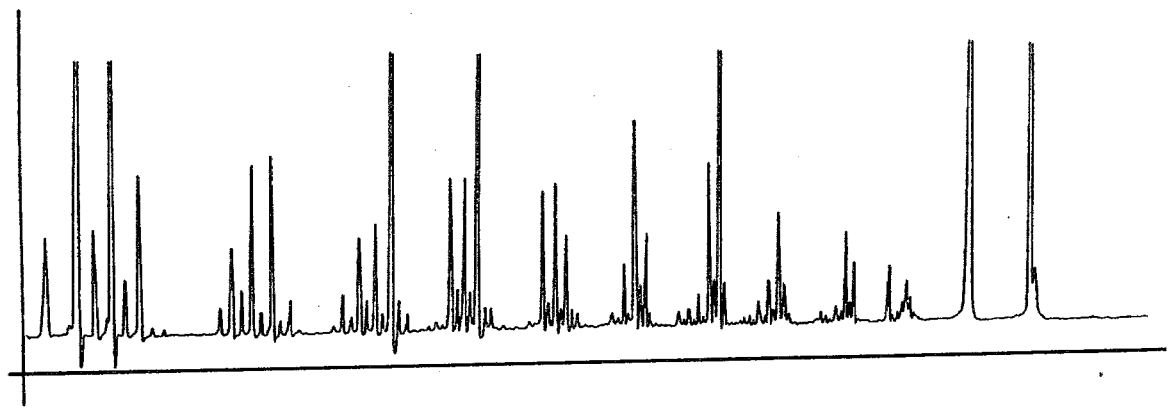

FIG. 17 is the mass spectrum for peak 3 of the GLC profile of the reaction product of this example which is compound having the structure:

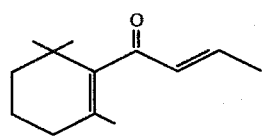

Figure 18:
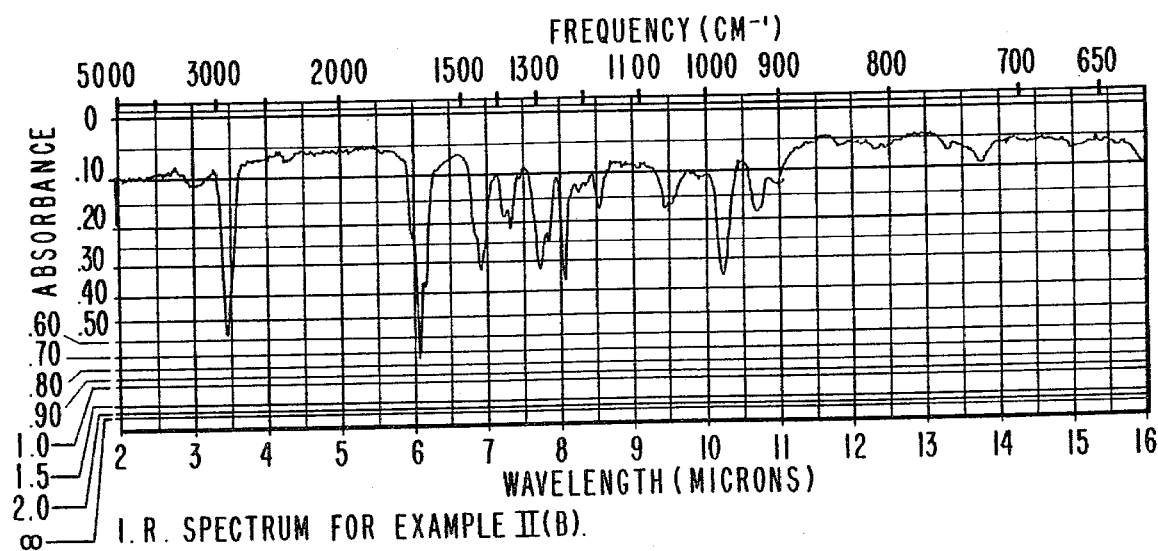
FIG. 18 is the infrared spectrum for peak 3 of the GLC profile of the reaction product of Example II(A).

FIG. 18 is the infrared spectrum for peak 3.

EXAMPLE II(b)

To a 25 ml reaction flask equipped with thermometer, hydrogen addition line and magnetic stirrer is added 0.5 grams of damascenone having the structure:

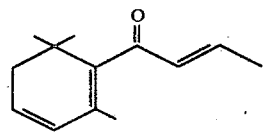

25 mg of palladium-on-barium sulfate (5% palladium) and 10 ml of ethyl acetate. The mixture is stirred and 0.25 mg of quinoline is added. The mixture is reduced with hydrogen (at 29°-30° C. and 1 atmosphere pressure) until an uptake of 130 ml is accomplished. During reduction the molecular weight of damascenone is monitored until the complete disappearance thereof. On analysis 16% by weight of a compound having the structure:

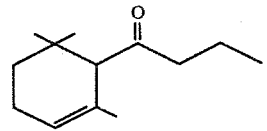

and 40% of the compound having the structure:

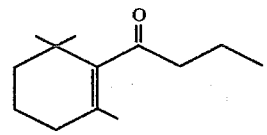

is produced. The quinoline is removed by means of washing with 10% aqueous hydrochloric acid followed by neutralization with a saturate sodium chloride solution (three 20 ml washed). The resulting mass is then dried over anhydrous magnesium sulfate and the ether is removed yielding 0.4 grams.

EXAMPLE II(c)

A system for carrying out hydrogenation is set up with a 1,000 cc flask equipped with thermometer, septum for purging and taking of samples, a hydrogen source and a biuret for measurement of hydrogen uptake. The flask contains a magnetic stirring bar.

The reaction flask is charged with beta damascenone (50 grams; 0.26 moles) 1.25 grams of a 5% palladium-on-barium sulfate catalyst; 500 ml ethyl acetate and 1.25 grams of quinoline.

The hydrogen is added slowly 100 cc at a time and monitored by means of GLC analysis, while maintaining the temperature at 25° C. at a pressure of one atmosphere.

A total of 5,566 ml hydrogen is used. The final GLC analysis indicates the presence of isomers having the following structures:

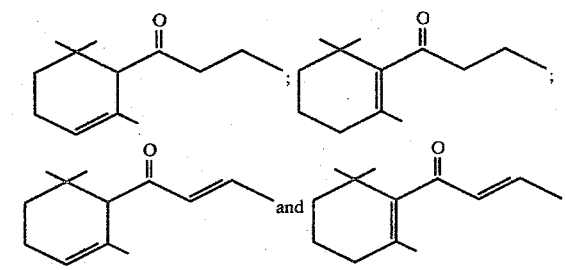

The reaction mass is filtered whereby the catalyst is gravity filtered out. The catalyst is washed several times with ethyl acetate and the ethyl acetate washing are added to the supernatant liquid.

The reaction mass is then passed through a column packed with silica gel to remove any extra catalyst.

The reaction mass is then washed with two 100 ml portions of 4% aqueous hydrochloric acid in order to wash out the quinoline. The reaction mass is then washed with four 50 ml portions of saturated sodium chloride. The reaction mass is then dried using anhydrous magnesium sulfate and filtered.

The reaction mass is then placed in a 500 ml receiver and a solvent is evaporated on a rotary evaporator yielding 53.5 grams of product. The product is then rushed over in a rotary evaporator yielding 53.5 grams of product. The product is then rushed over in a microdistillation setup yielding the following fractions:

| Fraction No. | Vapor Temp. (°C.) | Liquid Temp. | Vacuum mm. Hg. | Reflux Ratio | Weight of Fraction (grams) |
| --- | --- | --- | --- | --- | --- |
| 1 | 75/76 | 83/85 | .25/.25 | 1:00/1:05 | 1.2 |
| 2 | 77 | 86 | .25 | 1:15 | 1.3 |
| 3 | 80 | 86 | .25 | 1:18 | 1.8 |
| 4 | 50 | 101 | .25 | 1:22 | .7 |
| 5 | 88 | 91 | .25 | 1:45 | 1.3 |
| 6 | 112 | 110 | .15 | 2:40 | 1.8 |
| 7 | 72 | 96 | 0.135 | 3:05 | 1.9 |
| 8 | 82 | 97 | 0.133 | 3:11 | 8.9 |
| 9 | 86 | 99 | 0.133 | 3:16 | 9.3 |
| 10 | 86 | 105 | .133 | 3:27 | 10.3 |
| 11 | 79 | 128 | .133 | 3:35 | 7.5 |
| 12 | 62 | 205 | 0.125 | 17:45 | 0.6 |
| | | | | | 46.6 |

EXAMPLE III

Otto of Rose Perfume Formulation

The following mixture is prepared:

| Ingredients | Parts by Weight |
| --- | --- |
| Phenyl acetic acid | 5 |
| Hydrocycitronellal | 10 |
| Geraniol | 125 |
| Citronellol | 150 |
| Phenyl ethyl alcohol | 50 |
| Phenyl ethyl acetate | 4 |
| Ethyl phenyl acetate | 5 |
| Citronellyl formate | 20 |
| Geranyl acetate | 25 |
| Linalool | 15 |
| Terpineol | 10 |
| Eugenol | 3 |
| Phenyl acetaldehyde dimethyl acetal | 5 |
| Benzyl acetate | 3 |
| Guaiacwood Oil | 5 |
| 3-methylthio-4-heptanone produced according to the process of Part "C" of Example I of U.S. Pat. No. 4,065,408 issued on 12/27/77 | |
| Bulked fractions 8-11 of the mixture of compounds having the structure of the product produced according to Example I: | 5 |

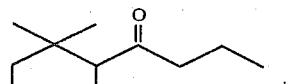

;

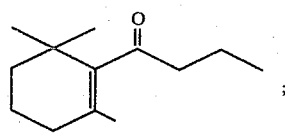

;

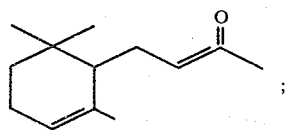

;

and

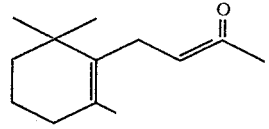

The hydrogenated beta damascenone mixture produced according to Example I used herein imparts to this Otto of Rose formulation floral and rose-like notes with heavy fruity (berry) nuances and in addition hay and slightly camphoraceous topnotes.

The use of the 3-methylthio-4-heptanone herein imparts a green, fruity, spicey topnote to this Otto of Rose perfume formulation. The combination of the 3-methylthio-4-heptanone together with the product produced according to Example I (bulked fractions 8-11 inclusive) causes the Otto of Rose perfume formulation to be much more "natural like".

When the mixture of Example I is replaced by the mixture of Example II(a), (b) or (c), the Otto of Rose perfume formulation is an "natural like" and has the same aroma nuances, topnotes and undertones as does the formulation containing the hydrogenation product of beta damascenone produced according to Example I.

EXAMPLE IV

Preparation of a Soap Composition

Chips of soap comprising 17% coconut fatty acid soap and 83% hydrogenated tallow acids sodium soap are mixed with titanium dioxide (a white pigment), preservative, the perfume composition of Example III and a bacteriostat in the proportions given below:

| Ingredient | Percent |
| --- | --- |
| 17:83 coco:tallow sodium soap chips | 95:85 |
| Titanium dioxide | 0.50 |
| Preservative | 0.15 |
| Perfume composition prepared according to Example III | 1.50 |
| Bacteriostat | 1.00 |

The soap chips, white pigment, preservative, perfume composition prepared according to Example III and bacteriostat are mixed and milled. The milled chips are fed into the top worn of a 4" double-barrel vacuum plodder.

After the segments pass through the die plate as described in the drawings of United Kingdom Pat. No. 1,494,278, a 10% aqueous dispersion of a blue pigment (Monastral Green GWD available from E. I. duPont deNemours, United States—"Monastral" is a registered trademark) is sprayed onto the segments at a predetermined rate of about half a pound of pigment dispersion per 100 pounds of soap.

The die plate used has circular holes each having a diameter of 1.25 inches and is more particularly described in Example I of United Kingdom Pat. No. 1,494,278. The knife has four blades and is rotated at a sufficient speed to produce segments 2 inches long. The geometric ratio is 5. The final soap bar has a distinct marbled appearance with an undiluted white background, bright blue colored areas and a clear demarcation between the white and blue areas. The resulting soap also has an excellent Otto of Rose-type aroma with distinct floral and heavy fruity undertones and hay and slightly camphoraceous topnotes.

EXAMPLE V

Preparation of a Soap Composition 100 grams of soap chips prepared according to Example IV but without any perfume added, is mixed with 1 gram of the bulked fractions 8–11 of the hydrogenated beta damascenone mixture produced according to Example I until a substantially homogeneous composition is obtained. The perfumed heterogeneous mixture is then heated to a temperature of 150° C. and maintained at that temperature for a period of 20 minutes. The mixture is then molded into a soap bar and permitted to cool to room temperature. The resulting soap bar has an excellent floral, rose-like aroma with heavy fruity (berry) nuances and hay and slightly camphoraceous topnotes.

When the mixture of Example I is replaced by the mixture prepared according to Examples II (a), (b) or (c) or when the mixture of Example I is replaced by the compound having the structure:

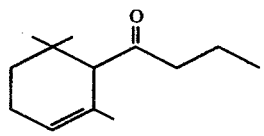

the resulting soap has very similar aromas to that produced when using the bulked fractions 8–11 prepared according to Example I. However, the compound having the structure:

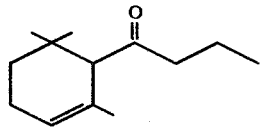

also imparts sweet, dry, fruity aroma nuances with hay tobacco undertones in addition to the aroma nuances set forth above.

EXAMPLE VI

Preparation of a Detergent Composition

A total of 100 grams of a detergent powder (a non-ionic detergent powder containing a proteolytic enzyme prepared according to Example I of Canadian Pat. No. 985,190 issued on Mar. 9, 1976) is mixed with 0.10, 0.15, 0.20, 0.25, or 0.30 grams of the mixture of hydrogenated derivatives of beta damascenone prepared according to Example I (bulked fractions 8–11) until a substantially homogeneous composition is obtained. The composition has an excellent floral, rose-like aroma with a heavy fruity (berry) undertone and hay and slightly camphoraceous topnotes.

When this mixture (bulked fractions 8–11 of Example I) is replaced by the compound having the structure:

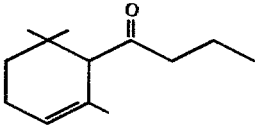

the resulting detergent has an excellent sweet, dry, fruity, floral aroma with hay tobacco nuances. When this compound is replaced by the "beta isomer" having the structure:

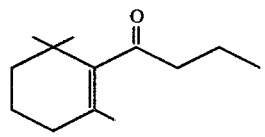

a sweeter, more tobacco aroma is produced in the detergent with deeper floral nuances.

EXAMPLE VII

A total of 100 grams of a detergent powder (a non-ionic detergent powder containing a proteolytic enzyme prepared according to Example I of Canadian Pat. No. 985,190 issued on Mar. 9, 1976) is mixed with 0.10, 0.15, 0.20, 0.25, or 0.30 grams of the perfume composition prepared according to Example III until a substantially homogeneous composition is obtained. This composition has an excellent Otto of Rose aroma with floral, heavy fruity nuances and hay and slightly camphoraceous topnotes.

EXAMPLE VIII

Perfumed Liquid Detergents

Concentrated liquid detergents with rich, pleasant Otto of Rose aromas are prepared containing 0.10%, 0.15%, 0.20%, 0.25% or 0.30% of the mixture prepared according to Example III. They are prepared by adding and homogeneously admixing the appropriate quantity of the composition of Example III in the liquid detergent. The liquid detergents are all produced using anionic detergents containing a 50:50 mixture of sodium lauroyl sarcosinate and potassium N-methyl lauroyl tauride. The detergents all possess a pleasant Otto of Rose fragrance with floral and heavy fruity undertones and hay and slightly camphoraceous topnotes.

EXAMPLE IX

Perfumed Liquid Detergents

Concentrated liquid detergents with rich, floral, rose-like aromas and fruity undertones and hay and camphoraceous topnotes are prepared containing 0.10%, 0.15%, 0.20%, 0.25%, 0.30% and 0.50% of the hydrogenated beta damascenone mixture prepared according to Example I (bulked fractions 8–11). They are prepared by adding and homogeneously admixing the appropriate quantity of hydrogenated beta damascenone mixture (bulked fractions 8–11 prepared according to Example I) in the liquid detergent. The liquid detergents are all produced using anionic detergents containing a 50:50 mixture of sodium lauroyl sarcosinate and potassium N-methyl lauroyl tauride. The detergents all possess a pleasant fragrance with floral, rose-like, heavy fruity (berry) aromas and hay and slightly camphoraceous topnotes. When the mixture of Example I (bulked fractions 8–11) is replaced by the compound having the structure:

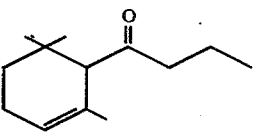

the detergents all possess excellent fruity, floral aromas with hay tobacco nuances. When this compound is replaced with the compound having the structure:

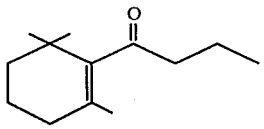

the resulting detergents have sweeter, more tobacco aromas and much deeper floral undertones.

EXAMPLE X

Handkerchief Perfume and Cologne Preparation

The perfume composition described in Example III is incorporated in colognes at concentrations of 2.0%, 2.5%, 3.0%, 4.0% and 5.0% in 85% aqueous food grade ethanol; and into handkerchief perfumes at concentrations of 15%, 20%, 25%, 30% and 40% (in 95% aqueous food grade ethanol). Distinctive and definitive strong otto of rose fragrances with floral, rose-like and heavy fruity nuances and hay and slightly camphoraceous topnotes are produced in the colognes and handkerchief of perfumes.

EXAMPLE XI

Handkerchief Perfume and Cologne Preparation

The hydrogenated beta damascenone mixture (bulked fractions 8–11) prepared according to Example I is incorporated into colognes at concentrations of 1.0%, 1.5%, 2.0%, 2.5%, 3.0%, 3.5% and 4.0% in 85% aqueous food grade ethanol; and into handkerchief perfumes at concentrations of 10%, 15%, 20% and 25% (in 95% aqueous food grade ethanol). Distinctive and definitive floral, rose-like aromas with heavy fruity (berry) undertones and hay and slightly camphoraceous topnotes are imparted to the cologne and to the handkerchief perfume. When the mixture of Example I (bulked fractions 8–11) is replaced with the compound having the structure:

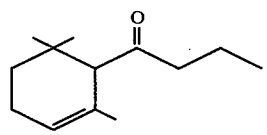

intense, fruity, floral aromas are produced in the handkerchief perfume and the cologne with hay tobacco nuances. When this compound is replaced with the compound having the structure:

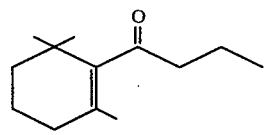

the resulting handkerchief perfume and colognes are both sweeter and more tobacco-like with deeper floral nuances.

EXAMPLE XII

Perfumed Shampoo

The hair cosmetic agents shown in Table I are incorporated into a base shampoo having the following composition:

| Ingredients | % By Weight |
|---|---|
| Ammonium lauryl sulphate | 18.0 |
| Lauric isopropanolamide | 1.0 |
| Texicryl 13–300 (Registered Trademark) | about 1.0 |
| Hair cosmetic agent of Table I | 1.0 to 12.0 |
| Color | 0.5 |
| Water | Balance to 100 |

Texicryl 13–300 (Trademark) is an aqueous emulsion of a carboxylated acrylic copolymer available from Scott Bader & Co. Ltd.

The amount of Texicryl 13–300 (Trademark) in the shampoo is adjusted according to the nature of the hair cosmetic agent used so that the viscosity of the shampoo is from 500 to 2,500 cps.

The pH of the shampoo is adjusted to 6.5 or greater.

TABLE I

| Example No. | Hair Cosmetic Agent | % By Weight in Base Shampoo |
|---|---|---|
| XII (A) | Ethoxylated lanolin | 2.0 |
|  | Glycerol monostearate | 2.0 |
| XII (B) | Long chain fatty condensate | 5.0 |
|  | Glycerol monostearate | 2.0 |
| XII (C) | Olive oil | 1.0 |
| XII (D) | Olive oil | 2.0 |
| XII (E) | Lanolin alcohol | 3.0 |
|  | Ethylene glycol monostearate | 1.0 |
| XII (F) | Lanolin alcohol | 4.0 |
|  | Ethylene glycol monostearate | 1.0 |

The long chain fatty condensate is an "Alcamine" resin supplied by Allied Colloids Ltd., Low Moor, Bradford, Yorks, England.

A second series of compositions is formulated by incorporating the hair cosmetic agents shown in Table 2 into the above base shampoo.

In an amount of 1% (1 part by weight per 100 parts by weight of shampoo), the hydrogenated beta damascenone (bulked fractions 8–11) produced according to Example I is added to the shampoo of each of Examples XII (A), (B), (C), (D), (E), and (F). To each of the shampoos, an excellent floral, rose-like aroma with a heavy fruity (berry) undertone and hay and slightly camphoraceous topnotes is imparted.

When the mixture produced according to Example I is replaced with a compound having the structure:

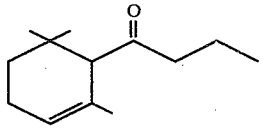

at a rate of 1% in the shampoo, the resultant shampoo has a fruity, floral aroma with tobacco undertones.

When this compound is replaced with 1.5% by weight of the compound having the structure:

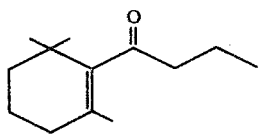

the resultant shampoos in each of Examples XII (A), (B), (C), (D), (E) and (F) have sweeter, more tobacco-like aromas with much deeper floral nuances.

EXAMPLE XIII

Raspberry Flavor Formulation

The following basic raspberry flavor formulation is produced:

| Ingredient | Parts by Weight |
| --- | --- |
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| | 1000.0 |

A mixture of compounds having the structures:

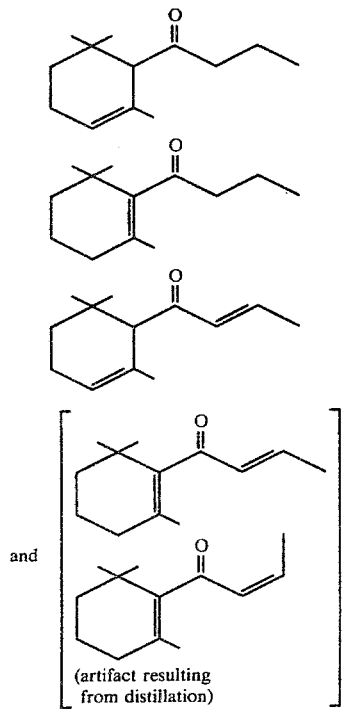

(8.9%)

(15.3%)

(12.2%)

(57.9%)

(artifact resulting from distillation)

prepared according to Example II is added to half of the above formulation at the rate of 0.02%. The formulation with the mixture of hydrogenated damascenones is compared with the formulation without the mixture of hydrogenated damascenones at the rate of 0.01% (100 ppm) in water and evaluated by a bench panel.

The flavor containing the hydrogenated damascenone mixture having the structures:

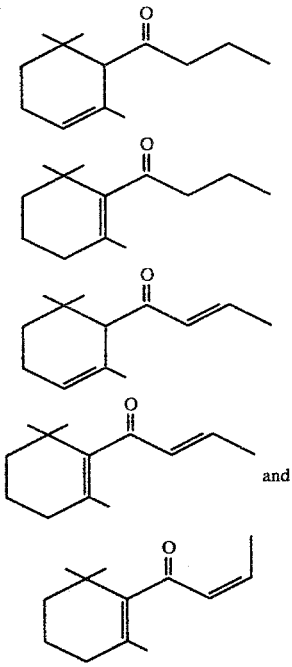

and is found to have a substantially more pleasant and better raspberry aroma. It is the unanimous opinion of the bench panel that the mixture of hydrogenated derivatives of damascenone having the structures:

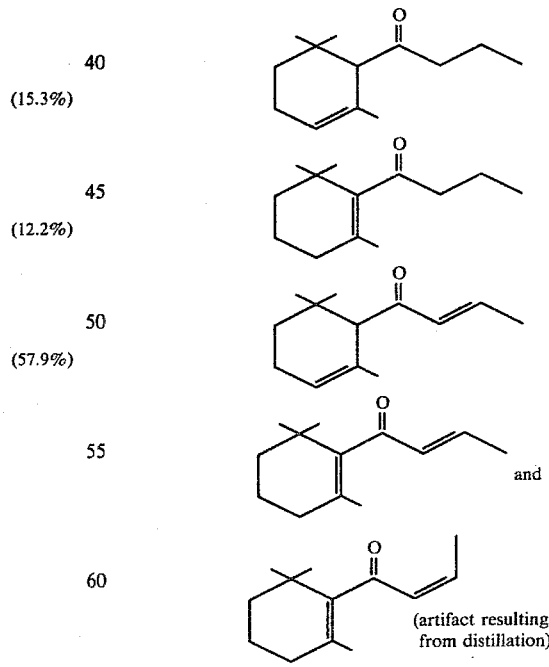

and (artifact resulting from distillation)

rounds the flavor out and contributes to a very natural fresh aroma and taste as found in full, ripe raspberries. Accordingly, the addition of the mixture of hydrogenated damascenones as described above is considered as substantially better than the flavor without said mixture of hydrogenated damascenones.

EXAMPLE XIV

Tobacco Formulation

A tobacco mixture is produced by admixing the following ingredients:

| Ingredients | Parts by Weight |
| --- | --- |
| Bright | 40.0 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 150 or 250 ppm. of the mixture produced according to Example II having the structures:

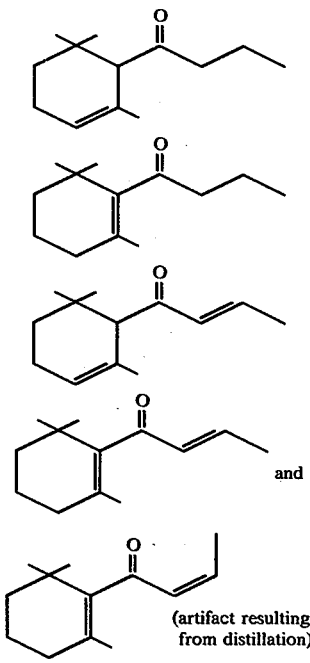

(artifact resulting from distillation)

(hereinafter referred to as hydrogenated damascenone mixture of Example II). The control cigarettes not containing the mixture of hydrogenated damascenone compounds produced according to the process of Example II and the experimental cigarettes which contain the mixture of hydrogenated damascenone compounds produced according to Example II are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with floral, sweet, fruity, hay, minty/spicey and woody aroma and taste nuances.

The tobacco smoke flavor of the experimental cigarettes, prior to smoking, has sweet, fruity, hay, musty, minty/spicey, and woody notes. All cigarettes are evaluated for smoke flavor with a 20 mm cellulose acetate filter.

When the mixture of hydrogenated damascenone derivatives is added to the filter rather than to the tobacco at either 50 ppm or 100 ppm, an interesting and pleasant sweet, fruity aroma is obtained prior to and on smoking the cigarettes.

EXAMPLE XV

Preparation of Cis Dihydro-Delta-Damascone

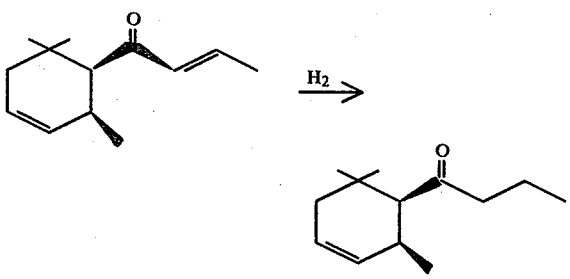

To a 250 ml microreaction flask equipped with magnetic stirrer, thermometer and hydrogen inlet tube is added 10 grams of cis,trans-delta-damascone prepared according to Example I of Application for U.S. Letters Patent, Ser. No. 851,727 filed on Nov. 15, 1977 (Dutch Application No. 78,09271 filed on Sept. 12, 1978).

100 ml Ethyl acetate and 0.25 grams of 5% palladium-on-barium sulfate and 0.25 grams of quinoline is then added. The mixture is then hydrogenated at atmospheric pressure at room temperature (20°–25° C.) until an uptake of 1400 ml of hydrogen is indicated. GLC analyses are run at about every 100 ml of hydrogen uptake. The reaction is caused to cease when no more delta-damascone is present. The catalyst is filtered off and the ethyl acetate evaporated leaving 8.5 grams of product. 150 ml anhydrous diethyl ether is then added and the solution of crude product is washed twice with a 4% aqueous hydrochloric acid solution (20 ml) and twice with a saturated sodium chloride solution (30 ml). The ether solution is then dried over anhydrous magnesium sulfate and evaporated leaving 8.0 grams of recovered material. This material is then distilled on a Naster-Faust spinning band column.

The resulting product has the structure:

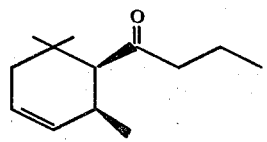

as confirmed by GLC, NMR and IR spectra as well as mass spectral analysis.

EXAMPLE XVI

Raspberry Flavor Formulation

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic Acid | 10.0 |
| Acetaldehyde | 10.0 |
| Propylene glycol | 930.0 |
| | 1000.0 |

A hydrogenated derivative of cis,trans-delta-damascone prepared according to Example XV having the structure:

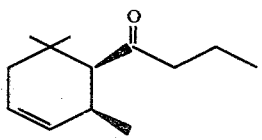

is added to half of the above formulation at the rate of 0.2%. The formulation with the hydrogenated derivative of cis,trans-delta-damascone is compared with the formulation without the hydrogenated derivative of cis,trans-delta-damascone at the rate of 0.01% (ppm) in water and evaluated by a bench panel.

The flavor containing the hydrogenated derivative of cis,trans-delta-damascone having the structure:

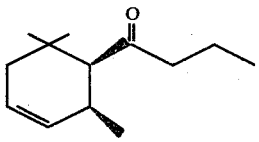

is found to have a substantially more pleasant and better raspberry aroma and taste. It also has the sweet, grape juice-like nuances so desired in fruit flavors. It is the unanimous opinion of the bench panel that the chemical having the structure:

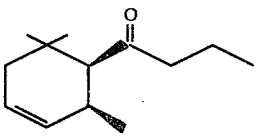

rounds the flavor out and contributes to a very natural, fresh aroma and taste found in full, ripe raspberries and, in addition, has the very interesting and useful grape juice nuance. Accordingly, the flavor with the addition of the hydrogenated derivative of cis,trans-delta-damascone is considered as substantially better than the flavor without said hydrogenated derivative.

EXAMPLE XVII

Preparation of Hydrogenated Product of Trans,Trans-Delta-Damascone

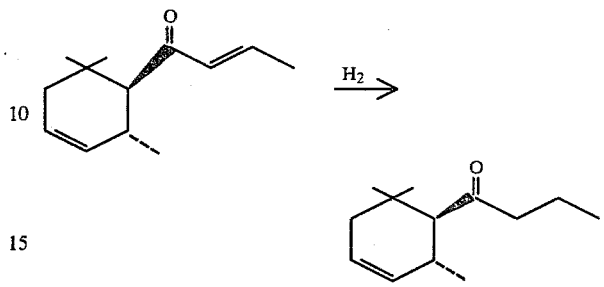

To a 500 ml reaction flask equipped with thermometer, and hydrogen addition tube and stirrer is added 50 grams of trans,trans-delta-damascone (prepared according to Example II of Application for U.S. Letters Patent Ser. No. 851,727 filed on Nov. 15, 1977, Dutch Application No. 78,09271 filed on Sept. 12, 1978), 1.85 grams of a 5% palladium-on-barium sulfate catalyst, 1.0 grams quinoline and 250 ml ethyl acetate. The resulting mixture is then hydrogenated (at atmospheric pressure and 20°–30° C.) until 5150 ml of hydrogen is absorbed. Mass spectra, IR and NMR analyses yield the information that the product having the structure:

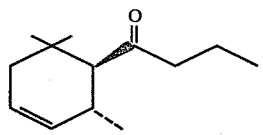

is formed.

Figure 19:
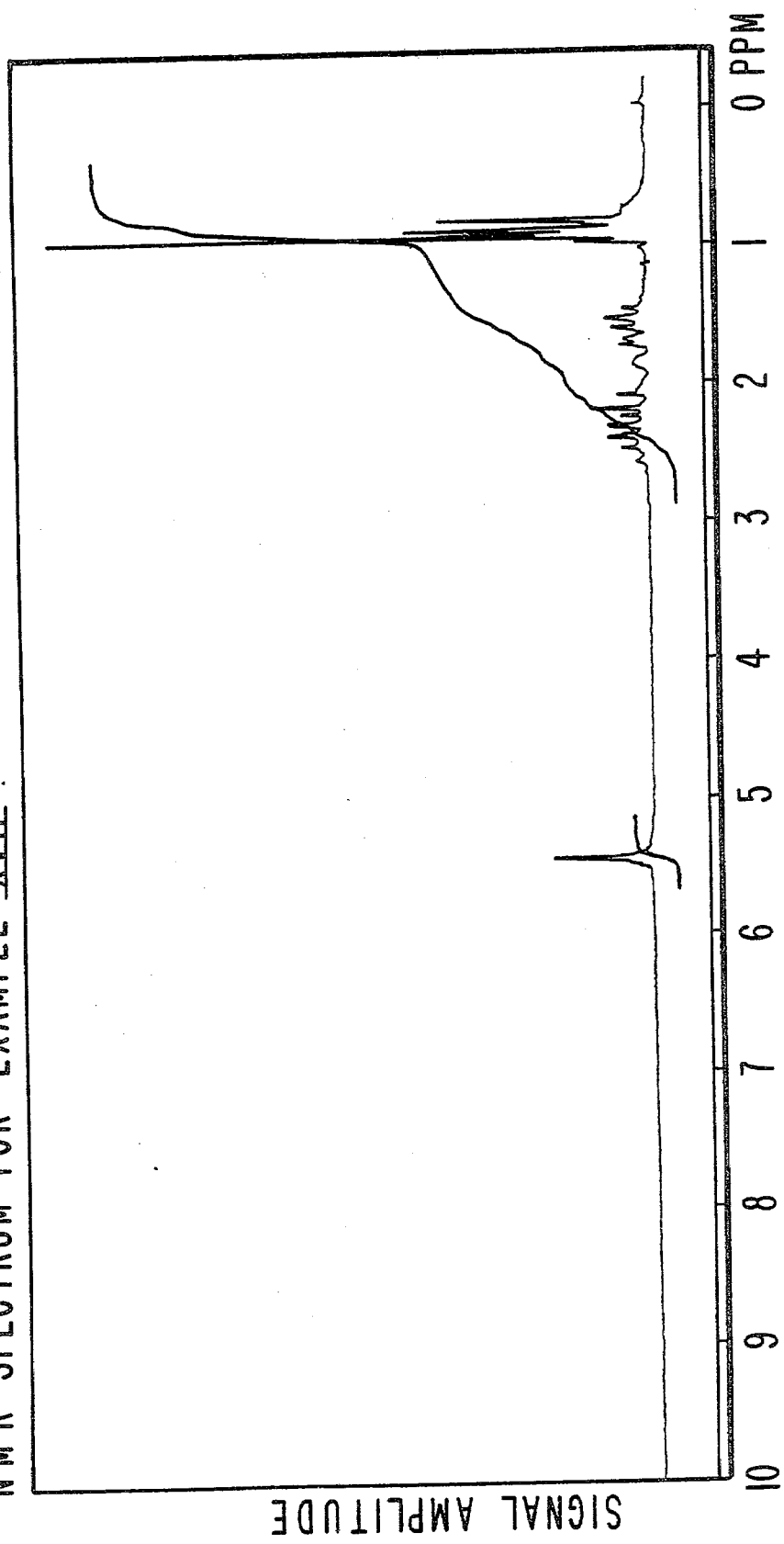
FIG. 19 is the NMR spectrum of the product produced according to Example XVII.

The ethyl acetate solution is then filtered to remove the catalyst and washed with two 20 ml volumes of 4% aqueous hydrochloric acid in order to remove the quinoline. The resulting solution is then washed with three 20 ml volumes of saturated sodium chloride and dried on anhydrous magnesium sulfate. After evaporation, 47.5 grams of crude product results which is distilled to yield 11 fractions. FIG. 19 is the NMR spectrum for the compound having the structure:

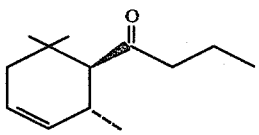

EXAMPLE XVIII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS 22 percent isopropyl alcohol
20 percent antistatic agent
1 percent of at least one butenoyl and/or butanoyl cyclohexane or cyclohexene compound or mixture thereof of our invention as set forth in the Table I below and giving rise to the aroma nuances as set forth in said Table I below:

TABLE I

| DESCRIPTION OF PERFUME INGREDIENT | FRAGRANCE CHARACTERISTICS |
|---|---|
| 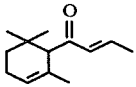 | At 1% in dipropylene glycol, a sweet, dry, fruity, floral aroma with hay tobacco nuances. |
| 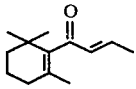 | A floral (rose) fruity (prune, berry-like) aroma. |
| 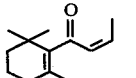 | A burnt, rosey aroma with weak floral nuances. |
| 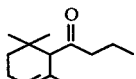 + 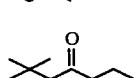 + 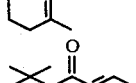 + 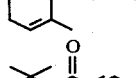 + 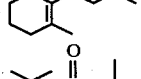 (mixture) | A floral, rose-like aroma with heavy fruity (berry) undertones; also hay and slightly camphoraceous nuances. (artifact resulting from distillation) |

Fabric-softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table I above are imparted in a pleasant manner to the head space in the dryer on operation thereof using the said dryer added fabric softening nonwoven fabric.

What is claimed is:
1. A dryer added fabric softener article comprising a substrate, coated on said substrate a coating and coated on said substrate coating an outer coating and intimately admixed with said outer coating at least one substance selected from the group consisting of:
(i) the compound having the structure:

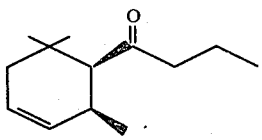

(ii) the compound having the structure:

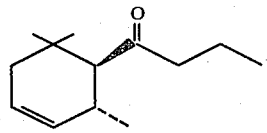

(iii) a mixture of compounds having the structures:

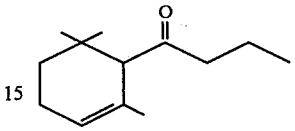

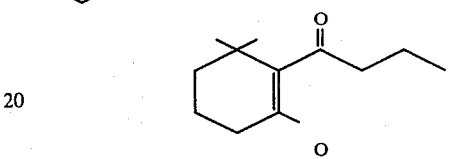

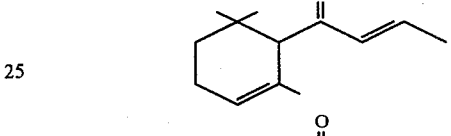

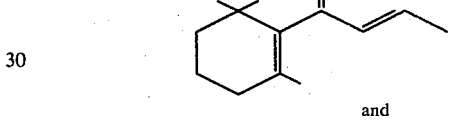

and

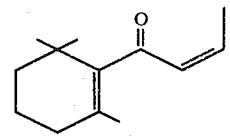

and (iv) a mixture of compounds having the structures:

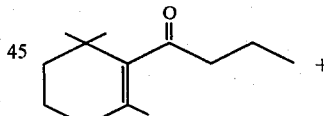 +

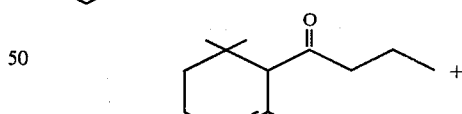 +

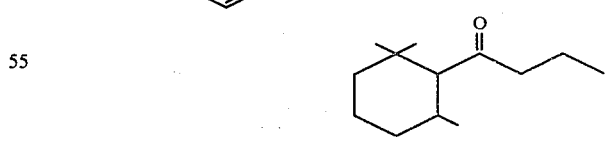

said substance being in such an amount that when the dryer-added fabric softener article is contacted with a clothing batch an aroma is imparted in a pleasant manner to the head space in the dryer on operation thereof using the said dryer-added fabric softening article.

2. A dryer-added fabric softener article comprising a substrate, coated on said substrate a substrate coating and coated on said substrate coating an outer coating and intimately admixed with said outer coating a product produced according to the process comprising the step of intimately admixing hydrogen with at least one compound defined by the structure:

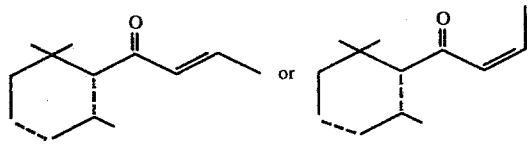

wherein in the cyclohexene moiety one of the dashed lines is a carbon-carbon double bond and the other of the dashed lines is either a carbon-carbon double bond or a carbon-carbon single bond, said reaction taking place in the presence of a suspended palladium catalyst, said product-by-process being present in said outer coating in such a quantity that when said dryer-added fabric softener article is in contact with a clothing batch in a dryer, an aroma is imparted in a pleasant manner to the head space in the dryer on operation thereof using the said dryer-added fabric softener article.

* * * * *